US012618801B2

(12) United States Patent
Schwartz et al.

(10) Patent No.: US 12,618,801 B2
(45) Date of Patent: May 5, 2026

(54) SYSTEM AND METHOD FOR PRESENTING LARGE DNA MOLECULES FOR ANALYSIS

(71) Applicants: Wisconsin Alumni Research Foundation, Madison, WI (US); Universiteit Leiden, EZ Leiden (NL); University of Chicago, Chicago, IL (US)

(72) Inventors: David C. Schwartz, Madison, WI (US); Kristy Kounovsky-Shafer, Kearney, NE (US); Juan Hernandez-Ortiz, Medellin (CO); Theo Odijk, Leiden (NL); Juan DePablo, Chicago, IL (US); Kyubong Jo, Seoul (KR)

(73) Assignees: Wisconsin Alumni Research Foundation, Madison, WI (US); Universiteit Leiden, EZ Leiden (NL); University of Chicago, Chicago, IL (US)

( * ) Notice: Subject to any disclaimer, the term of this patent is extended or adjusted under 35 U.S.C. 154(b) by 558 days.

(21) Appl. No.: 17/306,288

(22) Filed: May 3, 2021

(65) Prior Publication Data

US 2022/0291166 A1     Sep. 15, 2022

Related U.S. Application Data

(63) Continuation of application No. 14/485,119, filed on Sep. 12, 2014, now abandoned.
(Continued)

(51) Int. Cl.
*G01N 27/447*     (2006.01)
*B01L 3/00*     (2006.01)
(Continued)

(52) U.S. Cl.
CPC .. *G01N 27/44791* (2013.01); *B01L 3/502761* (2013.01); *G01N 27/3278* (2013.01);
(Continued)

(58) Field of Classification Search
CPC ........... C12Q 1/6867; G01N 27/44791; G01N 27/3278; G01N 33/48721
See application file for complete search history.

(56) References Cited

U.S. PATENT DOCUMENTS 8,105,471 B1 * 1/2012 Han ................. G01N 27/44752
                                                       204/601
8,940,148 B2     1/2015 Afzali-Azdakani et al.
(Continued)

FOREIGN PATENT DOCUMENTS

EP          261008 A1     7/2013

OTHER PUBLICATIONS

Kyubong Jo et al. "A single-molecule barcoding system using nanoslits for DNA analysis." Proceedings of the National Academy of Sciences 104.8 (2007): 2673-2678 (Year: 2007).*
(Continued)

*Primary Examiner* — Alexander S Noguerola
(74) *Attorney, Agent, or Firm* — Quarles & Brady LLP

(57)          ABSTRACT

Systems and methods for presenting nucleic acid molecules for analysis are provided. The nucleic acid molecules have a central portion that is contained within a nanoslit. The nanoslit contains an ionic buffer. The nucleic acid molecule has a contour length that is greater than a nanoslit length of the nanoslit. An ionic strength of the ionic buffer and electrostatic or hydrodynamic properties of the nanoslit and the nucleic acid molecule combining to provide a summed Debye length that is greater than or equal to the smallest physical dimension of the nanoslit.

18 Claims, 8 Drawing Sheets

Related U.S. Application Data

(60) Provisional application No. 61/877,570, filed on Sep. 13, 2013.

(51) Int. Cl.
*G01N 27/327* (2006.01)
*G01N 33/487* (2006.01)

(52) U.S. Cl.
CPC ................... *G01N 33/48721* (2013.01); *B01L 2200/0663* (2013.01); *B01L 2300/0816* (2013.01); *B01L 2300/0896* (2013.01)

(56) References Cited

U.S. PATENT DOCUMENTS

2002/0189948 A1* 12/2002 Minarik ........... G01N 27/44747
435/6.19
2008/0242556 A1* 10/2008 Cao ..................... G01N 21/6428
506/10
2011/0114486 A1 5/2011 Han
2011/0227558 A1 9/2011 Mannion et al.

OTHER PUBLICATIONS

Hsieh et al., "Ionic Effects on the Equilibrium Dynamics of DNA Confined in Nanoslits," Nano Letters 2008 vol. 8, No. 6, 1683-1688 ( Year: 2008).*

Karnik et al., "Effects of Biological Reactions and Modifications on Conductance of Nanofluidic Channels," Nano Letters 2005 vol. 5, No. 9, pp. 1638-1642 (Year: 2005).*

Ren et al., "Coulomb Forces on DNA Polymers in Charged Fluidic Nanochannels," Physical review Letters PRL 106, 068302 (2011) week ending Feb. 11, 2011 (Year: 2011).*

Zhang et al., "Effects of electrostatic screening on the conformation of single DNA molecules confined in a nanochannel," J. Chem. Phys. 128, 225109 (2008) (Year: 208).*

Reisner et al., "DNA confinement in nanochannels: physics and biological applications," Rep. Prog. Phys. 75 (2012) 106601 (Year: 2012).*

Krishna et al., "Spontaneous Stretching of DNA in a Two-Dimensional Nanoslit," Nano Letters 2007, vol. 7, No. 5, pp. 1270-1275 ( Year: 2007).*

Chang et al., "DNA conformation in nanochannels: Monte Carlo simulation studies using a primitive DNA model," The Journal of Chemical Physics 136,095101 (2012) (Year: 2012).*

Kim et al., "Nanochannel confinement: DNA stretch approaching full contour length," Lab Chip, 2011, 11, 1721 (hereafter "Kim"), Baumann et al., "Ionic Effects on the elasticity of single DNA molecules," Proc. Natl. Acad. Sci. USA vol. 94, pp. 6185-6190, Jun. 1997 Biophysics (Year: 2011).*

Li-Jing Cheng dissertation entiled "Ion and Molecule Transport in Nanochannels," Electrical Engineering and Computer Science in the University of Michigan, 2008 (Year: 008).*

Stein et al., "Surface-Charge-Governed Ion transport in nanofluidic Channels," Physical Review Letters vol. 93, No. 3, week ending Jul. 2004, pp. 035901-1 to 035901-4 (Year: 2004).*

Lee et al., "Electrically Tethered DNA Stretching in Nanochannels," Proceedings of the ASME 2009 International Mechanical Engineering Congress & Exposition IMECE2009 Nov. 13-19, Lake Buena Vista, Florida, USA (Year: 2009).*

Yeh et al., "Entropy-Driven Single Molecule Tug-of-War of DNA at Micro-Nanofluidc Interfaces," Nano Lett. 2012, 12, 1597-1602 (Year: 2012).*

O'Donnell et al., "Principles ad Concepts of DNA Replication in Bacteria, Archaea, and Eukarya," Cold Spring Harb Perspect Biol 2013;5:a010108 (Year: 2013).*

Salieb-Beugelaar et al., "Field-Dependent DNA Mobility in 20 nm High Nanoslits," Nano Letters vol. 8, No. 7, Jul. 2008 (Year: 2008).*

Balducci et al., "Elecrophoretic Stretching of DNA in Cross-Slot Nanoslit Channels," Macromoleucles 2008, 41, 9914-9918 (Year: 2008).*

Yang et al., "Stretching and selective immobilization of DNA in SU-8 micro- and nanochannels," J. Vac. Sci. Technol. B 25(6), Nov./Dec. 2007 (Year: 2007).*

Wang et al., "Simulation of DNA Extension in Nanochannels," Macromolecules 2011, 44, 6594-6604 (Year: 2011).*

Storm, Arnold J., et al. "Translocation of double-strand DNA through a silicon oxide nanopore." Physical Review E 71.5 (2005): 051903.

Strobl, Gert. "The physics of polymers: concepts for understanding their structure and behavior." Second Edition Springer-Verlag, Berlin (1997). (cover pages and table of contents only).

Sung, W., and P.J. Park. "Polymer translocation through a pore in a membrane." Physical review letters 77.4 (1996): 783.

Teague, Brian, et al. "High-resolution human genome structure by single-molecule analysis." Proceedings of the National Academy of Sciences 107.24 (2010): 10848-10853.

Tegenfeldt, Jonas O., et al. " The dynamics of genomic-length DNA molecules in 100-nm channels." Proceedings of the National Academy of Sciences of the United States of America 101.30 (2004): 10979-10983.

Turner, S. W. P., M. Cabodi, and H. G. Craighead. "Confinement-induced entropic recoil of single DNA molecules in a nanofluidic structure." Physical Review Letters 88.12 (2002): 128103.

Ullner, Magnus. "Comments on the scaling behavior of flexible polyelectrolytes within the Debye-Huckel approximation." The Journal of Physical Chemistry B 107.32 (2003): 8097-8110.

Underhill, Patrick T., and Patrick S. Doyle. "Alternative spring force law for bead-spring chain models of the work-like chain." Journal of Rheology (1978-present) 50.4 (2006): 513-529.

Underhill, Patrick T., and Patrick S. Doyle. "Development of bead-spring polymer models using the constant extension ensemble." Journal of Rheology (1978-present) 49.5 (2005): 963-987.

Underhill, Patrick, T., and Patrick S. Doyle. "On the coarse-graining of polymers into bead-spring chains." Journal of non-newtonian fluid mechanics 122.1 (2004): 3-31.

Valouev, Anton et al. "Alignment of optical maps." Journal of Computational Biology 13.2 (2006): 442-462.

Valouev, Anton, et al. "An algorithm for assembly of ordered restriction maps from single DNA molecules." Proceedings of the National Academy of Sciences 103.43 (2006): 15770-15775.

Valouev, Anton, et al. "Refinement of optical map assemblies." Bioinformatics 22.10 (2006): 1217-1224.

Vocks, Henk, et al. "Pore-blockade times for field-driven polymer translocation." Journal of Physics: Condensed Matter 20.9 (2008): 095224.

Vologodskii, Alexander and Nicholas Cozzarelli. "Modeling of long-range electrostatic interactions in DNA." Biopolymers 35.3 (1995): 289-296.

Wang, Yanwei, Douglas R. Tree, and Kevin D. Dorfman. "Simulation of DNA extension in nanochannels." Macromolecules 44.16 (2011): 6594-6604.

Yamakawa, Hiromi, and Motoharu Fujii. "Translational friction coefficient of worm-like chains." Macromolecules 6.3 (1973): 407-415.

Yeh, Jia-Wei, et al. "Entrophy-Driven Single Molecule Tug-of-War of DNA at Micro-Nanofluidic Interfaces." Nano etters 12.3 (2012): 1597-1602.

Abramoff, Michael D., Paulo J. Magalhaes, and Sunanda J. Ram. "Image processing with ImageJ." Biophotonics international 11.7 (2004): 36-43.

Allen, M.; Tildesley, D. Computer Simulation of Liquids; Oxford Science Publications: Oxford, U.K., 1987.

Antonacci, Francesca, et al. "A large and complex structural polymorphism at 16p12. 1 underlies microdeletion disease risk." Nature genetics 42.9 (2010): 745-750.

Banchio, Adolfo J., and John F. Brady. "Accelerated stokesian dynamics; Brownian motion." The Journal of chemical physics 118.22 (2003): 10323-10332.

(56) References Cited

OTHER PUBLICATIONS

Baumann, Christoph G., et al. "Ionic effects on the elasticity of single DNA molecules." Proceedings of the National Academy of Sciences 94.12 (1997): 6185-6190.

Brochard, F., and Pierre-Gilles de Gennes. "Dynamics of confined polymer chains." The Journal of Chemical Physics 67.1 (1977): 52-56.

Burkhardt, Theodore W. "Free energy o fa semi-flexible polymer in a tube and statistics of a randomly-accelerated particle." Journal of Physics A: Mathematical and General 30.7 (1997): 167-172.

Chanderasekhar, Subrahmanyan. "Stochastic problems in physics and astronomy." Reviews of modern physics 15.1 (1943): 1.

Chen, Y-L., et al. "Conformation and dynamics of single DNA molecules in parallel-plate slit microchannels." Physical Review E 70.6 (2004): 060901.

Chen, Y-L., et al. "DNA molecules inmicrofluidic oscillatory flow." Macromolecules 38.15 (2005): 6680-6687.

Chuang, Jeffrey, Yacov Kantor, and Mehran Kardar. "Anomalous dynamics of translocation." Physical Review E 65.1 (2001): 011802.

Cross, Joshua David, Elizabeth A. Strychalski, and H.G. Craighead. "Size-dependent DNA mobility in hanochannels." Journal of Applied Physics 102.2 (2007): 024701-024701.

Das, Somes K., et al. "Single molecule linear analysis of DNA in nano-channel labeled with sequence specific fluorescent probes." Nucleic acids research 38.18 (2010): e177-e177.

Demmel, James W., et al. "A supernodal approach to sparse partial pivoting." SIAM Journal on Matrix Analysis and Applications 20.3 (1999): 720-755.

Demmel, James W., John R. Gilbert, and Ziaoye S. Li. "An asynchronous parallel supemodal algorithm for sparse gaussian elimination." SIAM Journal on Matrix Analysis and Applications 20.4 (1999): 915-952.

Deserno, M., and C. Holm. "How to mesh up Ewald Shins." IA theoretical and nUlylerical comparison of varipus particle mesh routines. The Journal of Chemical Physics 109.181 (1998): 7678.

Deserno, Markus, et al. "Overcharging of DNA in the Presence of Salt: Theory and Simulation." The Journal of Physical Chemistry B 105.44 (2001): 10983-10991.

Dimalanta, Eileen T., et al. "A microfluidic system for large DNA molecule arrays." Analytical chemistry 76.18 (2004): 5293-5301.

Dimarzio, Edmund A., and Frank L. Mccrackin. "One-Dimensional Model of Polymer Adsorption." The Journal of Chemical Physics 43.2 (1965): 539-547.

Doi, M., and S. F. Edwards. "The theory of polymer dynamics. 1986." Claredon, Oxford. ISBN 0-19-852033-6 (1986).

Eisenriegler, E., K. Kremer, and K. Binder. "Adsorption of polymer chain at surfaces: Scaling and Monte Carlo analyses." The Journal of Chemical Physics 77.12 (1982): 6296-6320.

Essmann, Ulrich, et al. "A smooth particle mesh Ewald method." The Journal of Chemical Physics 103.19 (1995): 8577-8593.

Farkas, Zeno, Imre Derenyi, and Tamas Vicsek. "Dna uptake into nuclei: numerical and analytical results." Journal of Physics: Condensed Matter 15.18 (2003): S1767.

Farnoux, B., et al. "Cross-over in polymer solutions." Journal de Physique 39.1 (1978): 77-86.

Fixman, Marshall. "Construction of Langevin forces in the simulation of hydrodynamic interaction." Macromolecules 19.4 (1986): 1204-1207.

Fixman, Marshall. "Simulation of polymer dynamics. I. General theory. " The Journal of Chemical Physics 69.4 (1978): 1527-1537.

Frenkel, D.; Smit, B. Understanding Molecular Simulations: From Algorithms to Applications; Academic Press: San Diego, CA, 1996.

Gardiner, C. Handbook of Stochastic Methods; Springer: Berlin, 1985. (cover page and table of contents only).

Geier, Stephanie, Juan P. Hernandez-Ortiz, and Juan J. de Pablo. "Numerische Bestimmung der Durchgangsrate von Partikeln durch eine Porengeometrie." Chemie Ingeniur Technik 83.6 (2011): 900-906. (Enlish abstract).

Grassia, P. S., E. J. Hinch, and L. C. Nitsche. "Computer simulations of Brownian motion of complex systems." Journal of Fluid Mechanics 282 (1995): 373-403.

Hasimoto, H. "On the periodic fundamental solutions of the Stokes equations and their application to viscous flow past a cubic array of spheres." Journal of Fluid Mechanics 5.02 (1959): 317-328.

Hernandez-Ortiz, Juan P. "A Novel Approach for Electrokinetic Phenomena in Soft Matter." Dyna 79.175 (2012): 105-113.

Hernandez-Ortiz, Juan P., Christopher G. Stoltz, and Michael D. Graham. "Transport and collective dynamics in suspensions of confined swimming particles." Physical Review Letters 95.20 (2005): 204501.

Hernandez-Ortiz, Juan P., et al. "Concentration distributions during flow of confined flowing polymer solutions at finite concentration: slit and grooved channel." Korea-Aust. Rheol. J 20 (2008): 143-152.

Hernandez-Ortiz, Juan P., et al. "Cross-stream-line migration in confined flowing polymer solutions: Theory and simulation." Physics of Fluids (1994-present) 18.12 (2006): 123101.

Hernandez-Ortiz, Juan P., et al. "Hydrodynamic effects on the translocation rate of a polymer through a pore." The Journal of Chemical Physics 131.4 (2009):044904.

Hernandez-Ortiz, Juan P., Juan J. de Pablo, and Michael D. Graham. "Fast computation of many-particle hydrodynamic and electrostatic interactions in a confined geometry." Physical review letters 98.14 (2007): 140602.

Hernandez-Ortiz, Juan P., Juan J. de Pablo, and Michael D. Graham. "NlogN method for hydrodynamic interactions of confined polymer systems: Brownian dynamics." The Journal of Chemical Physics 125.16 (2006): 164906.

Hernandez-Ortiz, Juan P., Patrick T. Underhill, and Michael D. Graham. "Dyanmics of confined suspensions of swimming particles." Journal of Physics: Condensed Matter 21.20 (2009): 204107.

Herschleb, Jill, Gene Ananiev, and David C. Schwartz. "Pulsed-field gel electrophoresis." Nature protocols 2.3 (2007): 677-684.

Hockney, R. W.; Eastwood, J.W. Computer Simulation Using Particles; Taylor & Francis: Bristol, PA 1988. (cover page and table of contents only).

Hsieh, Chih-Chen, and Patrick S. Doyle. "Studying confined polymers using single-molecule DNA experiments." Korea-Australia Rheology Journal 20.3 (2008): 127-142.

Hsieh, Chih-Chen, Anthony Balducci, and Patrick S. Doyle. "Ionic effects on the equilibrium dynamics of DNA confined in nanoslits." Nano letters 8.6 (2008): 1683-1688.

Huang, Ziaohua, Manuel J. Gordon, and Richard N. Zare. "Current-monitoring method for measuring the electroosmotic flow rate in capillary zone electrophoresis." Analytical Chemistry 60.17 (1988): 1837-1838.

International Search Report and Written Opinion dated Feb. 11, 2015 for International patent application PCT/WO2014/055484.

Jendrejack, Richard M., et al. "DNA dynamics in microchannel." Physical review letters 91.3 (2003): 038102.

Jendrejack, Richard M., et al. "Effect of confinement on DNA dynamics in microfluidic devices." The Journal of Chemical Physics 119.2 (2003): 1165-1173.

Jendrejack, Richard M., et al. "Shear-induced migration in flowing polymer solutions: Simulation of long-chain DNA in microchannels." The Journal of Chemical Physics 120.5 (2004): 2513-2529.

Jendrejack, Richard M., Juan J. de Pablo, and Michael D. Graham. "Stochastic simulations of DNA in flow: Dynamics and the effects of hydrodynamic interactions." The Journal of Chemical Physics 116.17 (2002): 7752-7759.

Jendrejack, Richard M., Michael D. Graham, and Juan J. de Pablo. "Hydrodynamic interactions in long chain polymers: Application of the Chebyshev polynomial approximation in stochastic simulations." The Journal of Chemical Physics 113.7 (2000): 2894-2900.

Jo, Kyubong, et al. "A single-molecule barcoding system using nanoslits for DNA analysis." Proceedings of the National Academy of Sciences 104.8 (2007): 2673-2678.

Kantor, Yacov, and Mehran Kardar. "Anomalous dynamics of forced translocation." Physical Review E 69.2 (2004): 021806.

Kim, Yoori, et al. "Nanochannel confinement: DNA stretch approaching full contour length." Lab on a Chip 11.10 (2011): 1721-1729.

(56)  References Cited

OTHER PUBLICATIONS

Knotts IV, Thomas A., et al. "A course grain model for DNA." The Journal of Chemical Physics 126.8 (2007): 084901.

Locker, C. Rebecca, and Stephen C. Harvey. "A model for viral genome packing." Multiscale Modeling & Simulation 5.4 (2006): 1264-1279.

Locker, C. Rebecca, Stephen D. Fuller, and Stephen C. Harvey. "DNA organization and thermodynamics during viral packing." Biophysical Journal 93.8 (2007): 2861-2869.

Mannion, J. T., et al. "Conformational analysis of single DNA molecules undergoing entropically induced motion in nanochannels." Biophysical Journal 90.12 (2006): 4538-4545.

Marko, J. F., and E.D. Siggia. " Bending and twisting elasticity of DNA." Macromolecules 27.4 (1994): 981-988.

Marko, John F., and Eric D. Siggia. "Stretching DNA." Macromolecules 28.26 (1995): 8759-8770.

Mergell, Boris, Mohammad R. Ejtehadi, and Ralf Everaers. "Modeling DNA structure, elasticity, and deformations at the base-pair level." Physical Review E 68.2 (2003): 021911.

Mesoplasma florum Project Information from Broad Institute at http://www.broadinstitute.org/annotation/microbes/mesoplasma_florum/background.html.

Micheletti, Christian, and Enzo Orlandini. "Knotting and metric scaling properties of DNA confined in nano-channels: a Monte Carlo study." Soft Matter 8.42 (2012): 10959-10968.

Milchev, A., et al. "Ejection of a polymer chain from a nanopore: Theory and computer experiment." Macromolecules 43.16 (2010): 6877-6885.

Milchev, Andrey. "Single-polymer dynamics under constraints: scaling theory and computer experiment." Journal of Physics: Condensed Matter 23.10 (2011): 103101.

Miller, Clark A., et al. "Dipole-induced self-assembly of helical B-peptides." The Journal of Chemical Physics 129.1 (2008): 015102.

Mucha, Peter J., et al. "A model for velocity fluctuations in sedimentation." Journal of Fluid Mechanics 501 (2004): 71-104.

Odijk, Theo. "On the ionic-strength dependence of the intrinsic viscosity of DNA." Biopolymers 18.12 (1979): 3111-3113.

Odijk, Theo. "Polyelectrolytes near the rod limit." Journal of Polymer Science: Polymer Physics Edition 15.3 (1977): 477-483.

Odijk, Theo. "Scaling theory of DNA confined in nanochannels and nanoslits." Physical Review E77.6 (2008): 060901.

Odijk, Theo. "The statistics and dynamics of confined or entangled stiff polymers." Macromolecules 16.8 (1983): 1340-1344.

Orlandini, Enzo, and Cristian Micheletti. "Knotting of linear DNA in nano-slits and nano-channels: a numerical study." Journal of Biological Physics 39.2 (2013): 267-275.

Osswald, T. A.; Hernandez-Ortiz, J.P. Polymer Processing: Modeling and Simulation; Carl Hanser-Verlag: Munich, Germany, 2006. (cover pages and table of contents only).

Ottinger, Hans Christian. Stochastic processes in polymeric fluids: tools and examples for developing simulation algorithms. Springer Verlag, 1996. (cover pages and table of contents only).

Panja, Debabrata, Gerard T. Barkema, and Robin C. Ball. "Anomalous dynamics of unbiased polymer translocation through a narrow pore." Journal of Physics: Condensed Matter 19.43 (2007): 432202.

Petrov, Anton S., Krista LIM-HING, and Stephen C. Harvey. "Packaging of DNA by bacterioiphage epsilon 15: structure, forces, and thermodynamics." Structure 15.7 (2007): 807-812.

Popov, Konstantin I., et al. "Interacting nanoparticles with functional surface groups." Journal of Polymer Science Part B: Polymer Physics 50.12 (2012): 852-862.

Power, H.; Wrobell, L. C. Boundary Integral Methods in Fluid Mechanics; Computational Mechanics Publications: Southampton, U.K. 1995. (cover pages and table of contents only).

Pozrikidis, Constantine. Boundary integral and singularity methods for linearized viscous flow. Cambridge University Press, 1992. (cover pages and table of contents only).

Pranay, Pratik, et al. "Pair collisions of fluid-filled elastic capsules in shear flow: Effects of membrane properties and polymer additives." Physics of Fluids (1994-present) 22.12 (2010): 123103.

Press, W.H.; Teukolsky, S.A.; Vetterling, W.T.; Flannery, B.P. Numerical Recipes in Fortran 77, 2nd ed.; Cambridge University Press: Cambridge, U.K., 1992. ALT-Cover and TOC.

Reccius, Christian H., et al. "Conformation, length, and speed measurements of electrodynamically stretched DNA in nanochannels." Biophysical Journal 95.1 (2008): 273-286.

Reccius, Christian Hermann, et al. "Compression and free expansion of single DNA molecules in nanochannels." Physical review letters 95.26 (2005): 268101.

Reisner, Walter, et al. "Nanocinfinement-enhanced conformational response of single DNA molecules to changes in Ionic environment." Physical review letters 99.5 (2007): 058302.

Reisner, Walter et al. "Statics and dynamics of single DNA molecules confined in nanochannels." Physical Review Letters 94.19 (2005): 196101.

Risken, H., "The Fokker Planck Equation, Methods of Solution and Application 2nd Ed." (1989).

Rubinstein, M.; Colby, R. Polymer Physics; Oxford University Press: Oxford, U.K., 2003. (cover pages and table of contents only).

Salileb-Biugelaar, Georgette B., et al. "Field-dependent DNA mobility in 20 nm high nanoslits." Nano letters 8.7 (2008): 1785-1790.

Sambriski, E. J., D. C. Schwartz, and J.J. De Pablo. "A mesoscale model of DNA and its renaturation." Biophysical Journal 96.5 (2009): 1675-1690.

Sambriski, E. J., D. C. Schwartz, and J.J. De Pablo. "Uncovering pathways in DNA oligonucleotide hybridization via transition state analysis." Proceedings of the National Academy of Sciences 106.43 (2009): 18125-18130.

Sambriski, E.J., V. Ortiz, and J.J. De Pablo. "Sequence effects in the melting and renaturation of short DNA oligonucleotides: structure and mechanistic pathways." Journal of Physics: Condensed Matter 21.3 (2009): 034105.

Schwartz, David C., and Charles R. Cantor. "Separation of yeast chromosome-sized DNAs by pulsed field gradient gel electrophoresis." Cell 37.1 (1984): 67-75.

Biggia, E. D., et al. "Entropic elasticity of A—phage DNA." Science 265 (1994): 1599-1600.

Skolnick, Jeffrey and Marshall Fixman. "Electrostatic persistence length of a wormlike polyelectrolyte." Macromolecules 10.5 (1977): 944-948.

Stein, Derek, et al. "Electrokinetic concentration of DNA polymers in nanofluidic channels." Nano letters 10.3 (2010): 765-772.

Sternberg, Stanley R. "Biomedical image processing." Computer 16.1 (1983): 22-34.

Stigter, Dirk. "Interactions of highly charged colloidal cylinders with applications to double—stranded DNA." Biopolymers 16.7 (1977): 1435-1448.

Stigter, Dirk. "The charged colloidal cylinder with a Gouy double layer." Journal of Colloid and Interface Science 53.2 (1975): 293-306.

Stoltz, Christopher, Juan J. de Pablo, and Michael D. Graham. "Concentration dependence of shear and extensional rheology of polymer solutions: Brownian dynamics simulations." Journal of Rheology (1978-present) 50.2 (2006): 137-167.

Storm, A. J., et al. "Electron-beam-induced deformations of SiO2 nanostructures." Journal of Applied Physics 98.1 (2005): 014307.

Storm, Arnold J., et al. "Fast DNA translocation through a solid-state nanopore." Nano Letters 5.7 (2005): 1193-1197.

* cited by examiner

SYSTEM AND METHOD FOR PRESENTING LARGE DNA MOLECULES FOR ANALYSIS

CROSS-REFERENCE TO RELATED APPLICATIONS

This application is a continuation of U.S. application Ser. No. 14/485,119, filed Sep. 12, 2014, which application claims the benefit of U.S. Provisional Patent Application Ser. No. 61/877,570 filed on Sep. 13, 2013, the disclosure of which is incorporated by reference herein as if set forth in its entirety.

STATEMENT REGARDING FEDERALLY SPONSORED RESEARCH

This invention was made with government support under HG000225 awarded by the National Institutes of Health and 0832760 awarded by the National Science Foundation. The government has certain rights in the invention.

BACKGROUND OF THE INVENTION

The field of the invention is nucleic acid molecule manipulation. More particularly, the invention relates to stretching nucleic acid molecules in order to better present portions of the nucleic acid molecules for inspection by various techniques.

Much of the human genome is comprised of DNA sequences that are present in multiple copies. Although such elements play an important role in biological regulation and evolution, their presence troubles current DNA sequencing approaches. Accordingly, serious issues arise when trying to complete the sequencing of human, or cancer genomes because short analyte molecules, currently used by major sequencing platforms, often present redundant sequence data. Like trying to assemble a jigsaw puzzle with pieces bearing no uniquely discernible features, such sequence data make it difficult to assemble the sequence of an entire genome. Furthermore, our ability to assess genomic altera-tions within populations as mutations, or polymorphisms is also limited. To meet this challenge, genomewide analysis[1-3] systems are now featuring modalities that present large, genomic DNA analytes[3,4] for revealing genomic alterations through bioinformatic pipelines. Achieving utility for genome analysis using nanoconfinement approaches requires integration of system components that are syner-gistically poised for dealing with large data sets. Such components include sample preparation, molecular labeling, presentation of confined DNA molecules, and detection, complemented by algorithms incorporating statistical con-siderations of experimental error processes for data analy-sis.[5-8]

While a number of approaches to confine DNA molecules have been examined and implemented in the past few years,[5,19-15] few elongate DNA molecules close to their contour length. Kim et al.,[9] for example, elongated λ-DNA within poly(dimethylsiloxane) (PDMS) replicated nano-channels (250 nm×400 nm) and achieved a stretch of 0.88 using ultralow ionic strength conditions (0.06 mM). To our knowledge, it was the longest stretch reported for DNA molecules within nanochannels, using low ionic strength buffers. In different work, Reisner et al.[11] used 50 nm fused silica nanochannels with higher ionic strength conditions (~5 mM) to elongate DNA molecules up to 0.83. Although the stretch with these two approaches was higher than 0.8, both techniques exhibit limitations. The approach of Reisner et al. is demanding in that it requires fabrication of extreme nanoconfinement devices, smaller than the molecular per-sistence length,[16] to elongate DNA molecules close to the molecular contour length, thereby increasing the complexity of the molecular loading process.

Accordingly, a need exists for an approach to stretching a nucleic acid molecule that overcomes the aforementioned drawbacks.

SUMMARY OF THE INVENTION

The present invention overcomes the aforementioned drawbacks by providing a microfluidic device and a method of stretching a nucleic acid molecule.

In accordance with the present disclosure, the micro-fluidic device can include a first microchannel, a second microchannel, a nanoslit, a nucleic acid molecule, and an ionic buffer. The nanoslit can extend between the first and second microchannels. The nanoslit can provide a fluid path between the first and second microchannels. The nucleic acid molecule can include a first end portion, a second end portion, and a central portion positioned between the first end portion and the second end portion. The ionic buffer can be within the nanoslit and the first and second microchannel. The first microchannel can include a first cluster region adjacent to a first end of the nanoslit and the second microchannel can include a second cluster region adjacent to the second end of the nanoslit. The first cluster region can contain the first end portion. The second cluster region can contain the second end portion. The nanoslit can contain the central portion. The nucleic acid molecule can have a contour length that is greater than a nanoslit length of the nanoslit. An ionic strength of the ionic buffer and electro-static or hydrodynamic properties of the nanoslit and the nucleic acid molecule can combine to provide a summed Debye length that is greater than or equal to a nanoslit height or a nanoslit width. The nanoslit height or nanoslit width can be the smallest physical dimension of the nanoslit.

In accordance with the present disclosure, the method of stretching a nucleic acid molecule in an ionic buffer can include positioning the nucleic acid molecule such that a central portion of the nucleic acid molecule occupies a nanoslit, a first end portion of the nucleic acid molecule occupies a first cluster region adjacent to a first end of the nanoslit, and a second end portion of the nucleic acid molecule occupies a second cluster region adjacent to a second end of the nanoslit. The nanoslit, the first cluster region, and the second cluster region can include the ionic buffer. The nucleic acid can have a contour length that is greater than a length of the nanoslit. An ionic strength of the ionic buffer and electrostatic or hydrodynamic properties of the nanoslit and the nucleic acid molecule can combine to provide a summed Debye length that is greater than or equal to a nanoslit height or a nanoslit width. The nanoslit height or the nanoslit width can be the smallest physical dimension of the nanoslit.

The foregoing and other aspects and advantages of the invention will appear from the following description. In the description, reference is made to the accompanying draw-ings which form a part hereof, and in which there is shown by way of illustration a preferred embodiment of the inven-tion. Such embodiment does not necessarily represent the full scope of the invention, however, and reference is made therefore to the claims and herein for interpreting the scope of the invention.

DETAILED DESCRIPTION OF THE INVENTION

All referenced patents, applications, and non-patent literature cited in this disclosure are incorporated herein by reference in their entirety. If a reference and this disclosure disagree, then this disclosure is controlling.

This disclosure provides a micro-fluidic device. The microfluidic device can include a first microchannel, a second microchannel, a nanoslit, a nucleic acid molecule, and an ionic buffer. The nanoslit can extend between the first and second microchannels. The nanoslit can provide a fluid path between the first and second microchannels. The nucleic acid molecule can have a first end portion, a second end portion, and a central portion positioned between the first end portion and the second end portion. The ionic buffer can be within the nanoslit and the first and second microchannel. The first microchannel can include a first cluster region adjacent to a first end of the nanoslit and the second microchannel can include a second cluster region adjacent to the second end of the nanoslit. The first cluster region can contain the first end portion. The second cluster region can contain the second end portion. The nanoslit can contain the central portion. The nucleic acid molecule can have a contour length that is greater than a nanoslit length of the nanoslit. An ionic strength of the ionic buffer and electrostatic or hydrodynamic properties of the nanoslit and the nucleic acid molecule can combine to provide a summed Debye length that is greater than or equal to a nanoslit height or a nanoslit width. The nanoslit height or the nanoslit width can be the smallest physical dimension of the nanoslit.

This disclosure also provides a method of stretching a nucleic acid molecule in an ionic buffer. The method can include positioning the nucleic acid molecule such that a central portion of the nucleic acid molecule occupies a nanoslit, a first end portion of the nucleic acid molecule occupies a first cluster region adjacent to a first end of the nanoslit, and a second end portion of the nucleic acid molecule occupies a second cluster region adjacent to a second end of the nanoslit. The nanoslit, the first cluster region, and the second cluster region can include the ionic buffer. The nucleic acid can have a contour length that is greater than a length of the nanoslit. An ionic strength of the ionic buffer and electrostatic or hydrodynamic properties of the nanoslit and the nucleic acid molecule can combine to provide a summed Debye length that is greater than or equal to a nanoslit height or a nanoslit width. The nanoslit height or the nanoslit width can be the smallest physical dimension of the nanoslit.

Figure 1A:
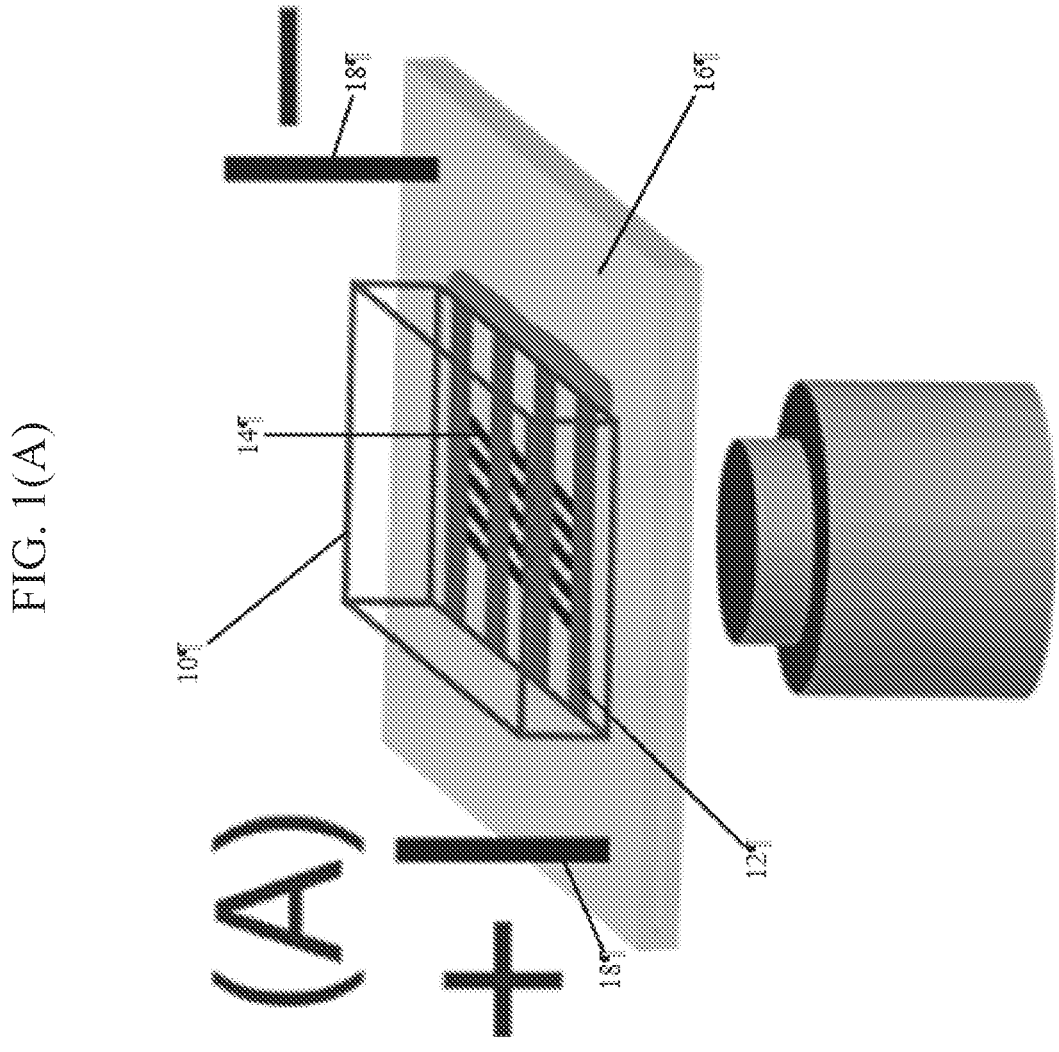
FIG. 1(A) shows microchannel-nanoslit device support-ing the formation of molecular dumbbells. PDMS device adhered to cleaned glass coverslip, immersed in buffer (not shown), for electrokinetic loading of DNA molecules.

Referring to FIG. 1(A), a micro-fluidic device can include a replica 10, such as a PDMS replica, including microchannels 12 and nanoslits 14. The device can be mounted on a substrate 16. The device can have electrodes 18.

Figure 1B:
FIG. 1(B) shows microchannel-nanoslit device supporting the formation of molecular dumbbells. Dumbbells form when loaded T4 DNA molecules (166 kb; 74.5 μm, dye adjusted contour length) exceed the nanoslit length (28 μm); molecule ends flanking nanoslits become relaxed coils within the microchannels (lobes), thereby enhancing the stretch of intervening segments within the nanoslits to (0.85±0.16, I=0.51 mM); traces show fluorescence intensity variations along molecular backbones.

Referring to FIG. 1(B), the microfluidic device can contain stretched nucleic acid molecules 20 in the dumbbell configuration. The fluorescence intensity 22 is shown next to the corresponding nucleic acid molecule 20. The lack of variation in fluorescence intensity 22 across the length of the nucleic acid molecule 20 indicates good stretching.

Figure 1C:
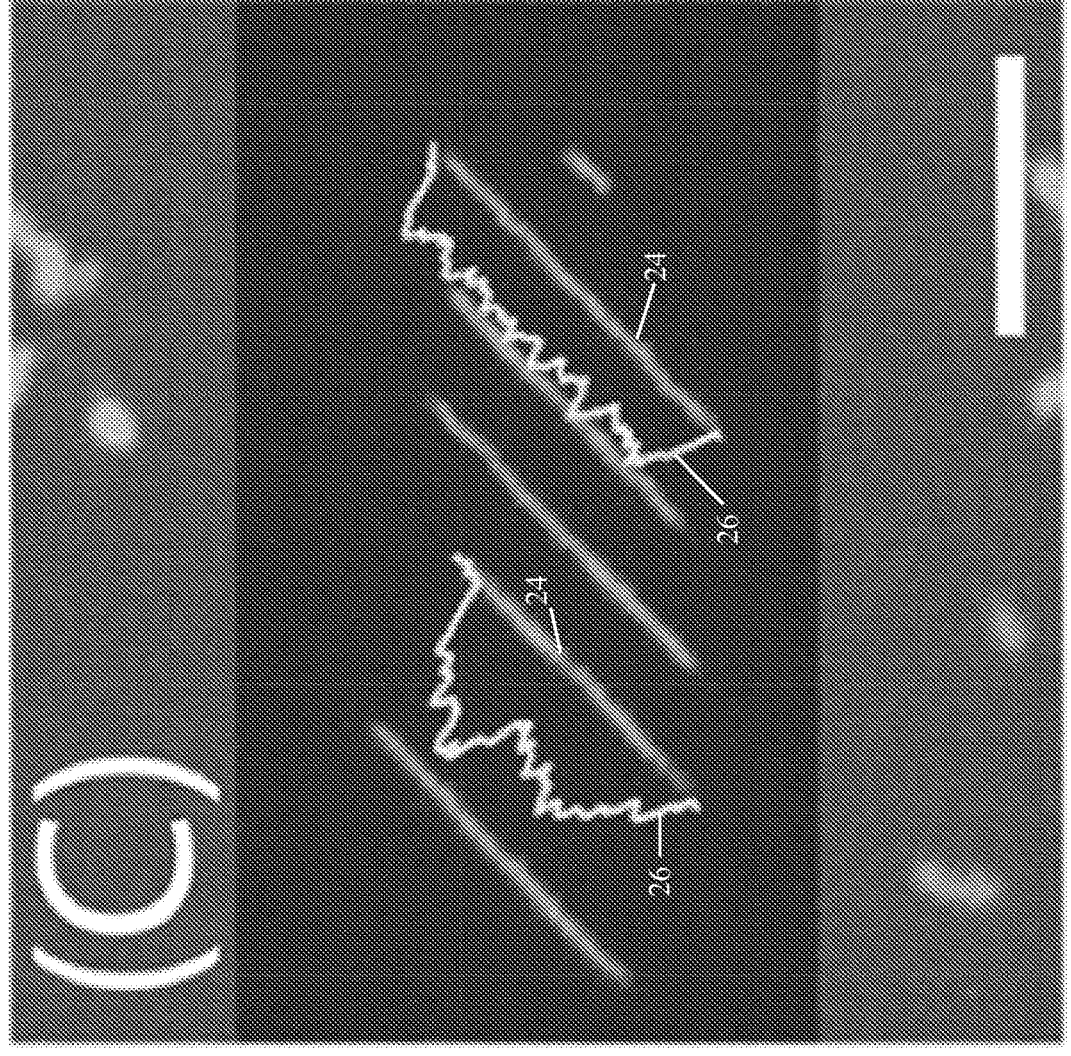
FIG. 1(C) shows microchannel-nanoslit device supporting the formation of molecular dumbbells. λ-DNA molecules (48.5 kb, 21.8 μm) are too short to form dumbbells and are thus completely confined within the nanoslits; a lower stretch (S/L=0.62±0.08, I=0.48 mM) is further evidenced by uneven fluorescence intensity profiles.

Referring to FIG. 1(C), the microfluidic device shown contains nucleic acid molecules 24 that are shorter than the nanoslit length, are not in the dumbbell configuration, and are not fully stretched. The fluorescence intensity 26 is shown next to the corresponding nucleic acid molecule. the larger variation in fluorescence intensity 26 across the length of the nucleic acid molecule 20 indicates poor stretching.

In certain embodiments, the nanoslit can be configured to contain a central portion of the nucleic acid molecule when the first cluster region holds a first clustered end portion of the nucleic acid molecule and the second cluster region holds a second clustered end portion of the nucleic acid molecule. The central portion of the nucleic acid molecule can be located generally between the first and second clustered ends of the nucleic acid molecule. As used herein, "clustered ends" or a "clustered configuration" refers to a configuration of the nucleic acid molecule that is not stretched out and contains random coils in at least a portion of the respective end of the nucleic acid molecule. As used herein, a "cluster region" refers to a space within a micro-channel that is occupied by a clustered end. The cluster region will inherently be the same size or smaller than its respective microchannel.

In certain embodiments, the nanoslit can have physical dimensions as follows. The nanoslit can have a smallest physical dimension that is on the order of 1 nm to about 1 μm. The nanoslit can have a nanoslit width of between 200 nm and 10 μm. The nanoslit can have a nanoslit width of less than or equal to 1 μm. The nanoslit can have a nanoslit length of less than or equal to 30 μm. The nanoslit can have a nanoslit height of between 20 nm and 200 nm. The nanoslit can have a nanoslit height of less than or equal to 100 nm. In certain embodiments, the nanoslit can have a substantially uniform nanoslit width, a substantially uniform nanoslit height, or both over the entire nanoslit length.

In certain embodiments, the nanoslit can have a length of less than or equal to a contour length of the nucleic acid molecule or less than or equal to half a contour length of the nucleic acid molecule.

In certain embodiments, the nanoslit can have a smallest physical dimension of at least 50 nm. In certain embodiments, the nucleic acid molecule is positioned in a nanoslit having a smallest physical dimension of at least about 50 nm. In other words, the device may not require that a cavity of less than 50 nm be fabricated. Moreover, when a nucleic acid molecule is positioned within, threaded through, or electrokinetically driven into a nanoslit of this embodiment, the smallest passage that it will encounter can be a passage of 50 nm.

In certain embodiments, the ionic buffer can have an ionic strength that suitably combines with the nanoslit and nucleic acid molecule to provide a summed Debye length that is greater than or equal to a nanoslit height or a nanoslit width, wherein the nanoslit height or nanoslit width is the smallest physical dimension of the nanoslit. In certain embodiments, the ionic buffer can have an ionic strength that provides a Debye length of the nanoslit or the nucleic acid that is at least about 25% of a nanoslit height or a nanoslit width, wherein the nanoslit height or nanoslit width is the smallest physical dimension of the nanoslit. In certain embodiments, the ionic buffer can have an ionic strength of less than or equal to about 0.75 mM.

In certain embodiments, the ionic buffer can include Tris-HCl, EDTA, 2-mercaptoethanol, POPE, or a combination thereof.

In certain embodiments, the ionic buffer can include a viscosity modifier. The viscosity modifier can be sucrose.

In certain embodiments, the first microchannel, the second microchannel, or both can have physical dimensions as follows. The microchannels can have a smallest physical dimension that is on the order of 1 μm to about 1 mm. The microchannels can have a microchannel width of between 1 μm and 1 mm. The microchannels can have a microchannel width of about 20 μm. The microchannels can have a microchannel length of between 100 μm and 20 cm. The microchannels can have a microchannel length of about 10 mm. The microchannels can have a microchannel height of between 20 nm and 100 μm. The microchannels can have a microchannel height of about 1.66 μm.

In certain embodiments, the device can further comprise a temperature adjustment module. The temperature adjustment module can be used to adjust the temperature of the nucleic acid molecule, the ionic buffer, or both. The temperature adjustment module can be used to raise or lower the temperature in order to slow the motion dynamics of the nucleic acid molecule. In certain embodiments, the ionic buffer can have a temperature of less than or equal to 20° C.

In certain embodiments, the micro-fluidic device can include one or more electrodes. The electrode or electrodes can be arranged substantially parallel to the nanoslit or nanoslits and can be used to electrokinetically drive the nucleic acid molecule into the nanoslit.

In certain embodiments, the nucleic acid molecule can have a relaxation time of at least about 30 seconds. In certain embodiments, the nucleic acid molecule can have a contour length that is greater than a nanoslit length of the nanoslit or at least two times greater than a nanoslit length of the nanoslit.

In certain embodiments, the nucleic acid molecule can be a DNA molecule.

In certain embodiments, positioning the nucleic acid molecule can include threading the nucleic acid molecule through the nanoslit, electrokinetically driving the central portion of the nucleic acid molecule into the nanoslit, or a combination thereof.

In certain embodiments, the methods can further include imaging at least a portion of the central portion of the nucleic acid molecule. Imaging can include microscopy, such as fluorescence microscopy, and the like.

As discussed throughout this disclosure, large DNA molecules may be presented for analysis in a "dumbbell" configuration. In the described approach, for example, a DNA molecule in an ionic buffer is caused to pass through a nanoslit within a micro-fluidic device. This may result in a configuration of the molecule in which a central portion of the molecule (i.e., a portion of the molecule within the nanoslit) is stretched toward a linear configuration and the opposite ends of the molecule (i.e., portions of the molecule outside the nanoslit) form a cluster configuration—i.e., a "dumbbell" configuration. Such presentation of DNA, in accordance with this disclosure, may take advantage of entropic, elastic and hydrodynamic forces to stretch the DNA, and may be useful, for example, in order to conduct various analyses on the stretched central portion of the relevant molecule (i.e., the "bar" of the dumbbell). To support such analyses, it may be useful to implement apparatus and procedures that ensure that the portion of the DNA molecule within a nanoslit reaches (or at least approaches) the "Odijk" regime (i.e., a noted plateau in the extension of a confined DNA molecule) and exhibits an appropriately long relaxation time, in order to facilitate execution of the desired protocol(s).

Through significant modeling and experimentation, it has been determined that notable improvement in the degree of stretch and the relaxation time of DNA molecules may be effected using carefully selected combinations of micro-fluidic device configurations and ionic solution characteristics. For example, use of a low strength ionic environment in conjunction with appropriately scaled nanoslits in a micro-fluidic device may facilitate achievement of a more fully stretched configuration of a subject DNA molecule than has been previously possible. Such environment/scaling may beneficially manage the delicate balance between electrostatic and hydrodynamic interactions responsible for conformations of the observed molecules.

As one example, it has been determined that micro-fluidic devices exhibiting nanoslit length of less than half the contour length of the relevant molecule may deliver relaxation time on the order of minutes, a marked improvement over molecules that do not employ the dumbbell configuration described herein. This may strongly facilitate experimental observation of the molecule. Accordingly, for certain applications, it may be beneficial to configure micro-fluidic devices with nanoslits having a length of no more than half of the contour length of a relevant DNA molecule. Notably, under certain configurations and conditions, once the nanoslit length has been appropriately adjusted with respect to a reference molecule, the same micro-fluidic device may be utilized for relatively uniform presentation of molecules of any size (e.g., molecules with contour lengths (L) exceeding the contour length of the reference molecule). For example, with respect to particular molecules (e.g., A bacteriophage (New England Biolabs) 48.5 kb (L=16.5 μm/21.8 μm), T4 bacteriophage (Wako Chemicals) 166 kb (L=56.3 μm/74.5 μm), λ-concatemers (New England Biolabs, A concatemer ladder, size range=137.4-582.0 kb), *M. florum* (Apal digest: 252 kb, L=85.7 μm/113.2 μm; 541 kb L=184.2 μm/243.2 μm), each in solution containing 4% (v/v) 2-mercaptoethanol, 0.1% (w/v) POPE (Applied Biosystems) and TE buffer (1×: 10 mM Tri-HCL and 1 mM EDTA pH 7.9) ranging from 0.01× to 0.1×) (L, above, indicates unstained/stained contour length, respectively), a micro-fluidic device may be beneficially fabricated to include 1 μm wide×100 μm high by 28 μm long nanoslits. In this way, the length of the nanoslits is generally less than half the (stained or unstained) contour length of the tested molecules and enhanced relaxation times may be achieved accordingly.

Micro-fluidic devices, such as those described above, may also include microchannels at either end of the noted nanoslits. In certain embodiments, the microchannels for the example device described above may be fabricated with dimensions of 20 μm wide×1.66 μm high×10 mm long. Fabrication of these micro-fluidic devices (and others contemplated by the disclosure) may utilize various known techniques, such as reactive ion etching on silicon wafers, with PDMS replicas being created by soft lithography and made hydrophilic by $O_2$ plasma treatment.

In addition or as an alternative to the above-described nanoslit configuration, the stretch of subject molecules may also be beneficially enhanced by providing the nucleic acid in a reduced ionic strength buffer. For example, in contrast to various current theories, it has been discovered that Odijk regime stretching may be obtained by providing effective confinement equal (or at least comparable) to the persistence length of a relevant DNA molecule (taking into account, in certain embodiments, electrostatic considerations). To this end, decrease of ionic strength may beneficially increase chain persistence lengths and enhanced effective confinement, which is induced by the increased Debye length of the micro-fluidic device's surface (itself also enhanced by appropriately low ionic strength). For example, reduced ionic strength and appropriately configured nanoslits may result in the Debye lengths of the device and/or the persistence length of the molecule being comparable (or equal) to nanoslit height (e.g., ~100 nm, for the device described above). In this way, because the effective confinement is comparable (or equal) to the chain persistence length, the Odijk regime may be achieved. Therefore, use of decreased ionic strength buffer with appropriate micro-fluidic device configurations (e.g., nanoslit dimensions) may result in longer relaxation times, thereby better facilitating imaging-based genomic analysis and other investigation. As such, it may be appropriate to design and fabricate micro-fluidic devices (e.g., with respect to nanoslit dimensions) and to select buffer ionic strength (e.g., with a view toward increasing Debye length) based upon the persistence length of the relevant DNA molecule, rather than (or in addition to) focusing on the effective DNA diameter. For example, with respect to the example device discussed above (i.e., with 1 μm wide×100 nm high by 28 μm nanoslits), a TE buffer may be utilized having final concentrations of 0.006% for 2-mercaptoethanol and 0.00015% for POPE.

As an additional measure, in certain embodiments, addition of sucrose to low ionic strength solutions (as discussed above) and/or an appropriately timed decrease of temperature may increase solution viscosity and thereby further extend relaxation time.

In practice, therefore, subject DNA may be threaded through nanoslits on a micro-fluidic device via timed electrical pulses, resulting in the above-described "dumbbell" configuration. As noted above, in certain embodiments, the nanoslits may be configured/manufactured based upon relevant characteristics of the DNA molecules (e.g., molecule contour length and/or persistence length), and an appropriately low ionic strength buffer may be utilized (e.g., 0.11 mM or similar strength, as necessary to provide a device Debye length comparable to nanoslit height). Notably, the lower ionic strength buffer (e.g., 0.11 mM), in combination with the appropriately scaled nanoslits and the elastic forces generated by the induced dumbbell configuration, may greatly enhance DNA elongation, even to the point of a fully stretched presentation. As also discussed throughout the disclosure, this enhancement may result, for example, from hydrodynamic interactions of the DNA dumbbells and entropic recoil of the dumbbell lobes as well as the enhancement of electrostatic interactions via reduced ionic strength conditions. In certain instances, sucrose may also be added to the low ionic solution and/or temperature may be decreased (e.g., shifted after loading) to increase solution viscosity and thereby further extend the relaxation time.

Past efforts using 250 nm×400 nm PDMS replicated nano-channels and 0.06 mM ionic strength buffer have delivered stretch of 0.88 for A DNA. The Debye length under these conditions is approximately 40 nm. Accordingly, the summed Debye length (the Debye length of the device roof, the device floor, the surface of the nucleic acid molecule facing the device roof, and the surface of the nucleic acid molecule facing the device floor, i.e., 4 times the Debye length) is about 160 nm, which is short of the smallest physical dimension of 250 nm. Likewise, efforts with 50 nm fused silica nano-channels and ~5 mM ionic strength buffer have delivered stretch of up to 0.83 for DNA molecules. The Debye length under these conditions is approximately 1.34 nm. Accordingly, the summed Debye length is about 5.34 nm, which is short of the smallest physical dimension of 50 nm. In contrast, use of one embodiment of the disclosed combination of appropriately scaled nanoslit dimensions (e.g., as tuned to relevant aspects of the target molecule) and appropriately low ionic strength buffers (e.g., as selected for enhanced scaling of the device Debye lengths) may usefully deliver stretch of 1.06 or higher.

The analysis of very large DNA molecules intrinsically supports long-range, phased sequence information, but requires new approaches for their effective presentation as part of any genome analysis platform. Using a multipronged approach that marshaled molecular confinement, ionic environment, and DNA elastic properties buttressed by molecular simulations we have developed an efficient and scalable approach for presentation of large DNA molecules within nanoscale slits. Our approach relies on the formation of DNA dumbbells, where large segments of the molecules remain outside the nanoslits used to confine them. The low ionic environment, synergizing other features of our approach, enables DNA molecules to adopt a fully stretched conformation, comparable to the contour length, thereby facilitating analysis by optical microscopy. Accordingly, a molecular model is proposed to describe the conformation and dynamics of the DNA molecules within the nanoslits; a Langevin description of the polymer dynamics is adopted in which hydrodynamic effects are included through a Green's function formalism. Our simulations reveal that a delicate balance between electrostatic and hydrodynamic interactions is responsible for the observed molecular conformations. We demonstrate and further confirm that the "Odijk regime" does indeed start when the confinement dimensions are of the same order of magnitude as the persistence length of the molecule. We also summarize current theories concerning dumbbell dynamics.

Here, electrokinetic loading of large DNAs into nanoslits offers new routes to stretching of random coils and presentation as analyte arrays. Nanoslits, or channels with aspect ratios >1, realize genomically scalable nanoconfinement conditions that facilitate acquisition of large data sets. Nanoslits also allow inexpensive fabrication through large-scale replication of disposable devices from electron-beam fabricated masters. Moreover, low-ionic strength conditions increase a DNA molecule's persistence length, thereby leading to nanoconfinement of DNA in devices that are compatible with the inherent geometric limitations of silastic materials.[5,9] In the first generation of "Nanocoding," the mapping of confined DNA molecules was carried out with sequence-specific labels.[5] The value of such mapping data for genomic analysis was shown to depend on marker density[6] and molecular stretch S/L (where S is the apparent length of a molecule and L is its contour length).

Through a concerted experimental and theoretical approach outlined in previous work,[5] we reasoned that engaging DNA "dumbbell" conformations within our nanoslits would greatly enhance DNA stretching through entropic, elastic, and hydrodynamic forces. In this paper, we define a DNA dumbbell as comprising two relaxed coils (lobes) within a microchannel flanking intervening polymer segments residing within a nanoslit (FIG. 1). Our experiments indeed show that molecular dumbbells increase DNA stretch within nanoslits up to the full molecule contour length using the same ionic strength and "spacious" confinement conditions (slit dimensions: 100 nm×1000 nm) as in previous experiments.[5] More importantly, DNA dumbbells overcome limitations of current approaches, including ionic strengths below 0.06 mM, or severe confinement (below 50 nm). A combination of the lobes' entropic recoil, hydrodynamic interactions, and electrostatic interactions, mediated by low-ionic strength conditions, produces tension across the DNA molecule backbone within the nanoslit, further elongating the molecule. For the first time, a dumbbell conformation allows the elongation of DNA molecules within nanoslits demonstrating stretch up to 1.06±0.19. Our results indicate that the "Odijk regime" is achieved once the persistence length is equal to the effective confinement (including electrostatic considerations), in apparent contradiction to other theories that suggested that the effective DNA diameter is the relevant parameter for the de Gennes- Odijk transition.[11] In addition, we find that once the contour length of the molecule is longer than twice the nanoslit length, the dumbbell's relaxation time is on the order of minutes, and increases with lobe size. The stretch remains independent of the molecular weight. Such molecular presentation greatly enhances the entrapment of stretched molecules (i.e., out-of-equilibrium metastable states), thereby making this approach a practical component for genome analysis systems.

Recently, Yeh et al.[17] also performed experiments on confined DNA molecules in combined micro- and nanoscale devices similar to those employed by Kim et al.[9] They observed that under some circumstances, long DNA was able to form dumbbells. They explained their observations in terms of quasistatic arguments, highlighting an entropy-driven single molecule tug-of-war (TOW) scheme that enables study of the statics and the dynamics of entropic recoil under strong confinement. In this work we show that this quasi-static regime, corresponding to symmetric lobes within the microscale confinement, has a vanishing probability of appearance. The confined molecules are under nonequilibrium conditions, and the uneven size of the lobes controls molecular recoil. By taking account of nonequilibrium conditions, we show that several mechanisms can control molecule dynamics and dumbbell lifetimes.

Materials and Experimental Methodology

Device Fabrication and Setup. Microchannel-nanoslit device masters were fabricated by electron beam lithography using the JEOL JBX-SDII system (CNTech, UW-Madison). Nanoslits (1 μm wide×100 nm high×28 μm long) were etched into a silicon wafer by CF4 reactive ion etching and modified SU8 microchannels (20 μm wide×1.66 μm high× 10 mm long) were overlaid (see FIG. 1). PDMS replicas were created by soft lithography, made hydrophilic by $O_2$ plasma treatment, and stored in distilled water for 24 h then the devices were utilized for a couple of months. Nanoslit devices were mounted on acid-cleaned negatively charged glass surfaces.[1] Platinum electrodes (wire, 0.013" diameter) were placed in a diagonal orientation, nearly parallel to the nanoslits, in the buffer chamber, a glass surface affixed to the bottom of a Plexiglas holder, and attached to Kepco (model BOP 100-1M) bipolar operational power supply. DNA solutions were loaded into the microchannels using capillary action, and devices were immersed in buffer [TE with final concentrations of 2-mercaptoethanol (0.006%) and POP6 (0.00015%; Applied Biosystems)] for 20 min, allowing buffer equilibration before measurements. After the device is immersed, DNA molecules were electrokinetically driven into the nanoslits, timed before they completely exited, so that they were trapped as dumbbells.

DNA Samples and Stretching. DNA samples, stained with YOYO-1 (1,1-[1,3-propanediylbis[(dimethyliminio)-3,1-propanediyl]]bis[4-[(3-methyl-2 (3H) benzoxazolylidene) methyl]-quinolinium iodide)[5] (Molecular Probes), included [(unstained/stained contour length), L; assuming an intercalation rate of 1 dye/4 bp] λ-bacteriophage (New England Biolabs) 48.5 kb (L=16.5 μm/21.8 μm), T4 bacteriophage (Wako Chemicals) 166 kb (L=56.3 μm/74.5 μm), λ-concatemers (New England Biolabs, A concatemer ladder, size range=137.4-582.0 kb), *Mesoplasma florum* (Apal digest: 252 kb, L=85.7 μm/113.2 μm; 541 kb, L=184.2 μm/243.2 μm. DNA solutions also contained 4% (v/v) 2-mercaptoethanol, 0.1% (w/v) POP6 (Applied Biosystems) and TE buffer (1×: 10 mM Tris-HCl and 1 mM EDTA pH 7.9) ranging from 0.01× to 0.1×; ionic strength was determined by conductivity using a NaCl standard.[5]

Image Capture and Analysis. YOYO-1-stained molecules were imaged (Manual Collect softwares) using a Hamamatsu CCD camera (Orca-ER), coupled to a Zeiss 135 M epifluorescence microscope (63× Zeiss Plan-Neofluar oil immersion objective), illuminated by an argon ion laser (488 μm; 8 nW to 200 nW measured at nosepiece) for stretch and relaxation time experiments. A more sensitive camera (Andor iXon-888 EMCCD) was used to image the relaxation kinetics of T4 dumbbell molecules. Images were analyzed using ImageJ[18] to subtract background using the "rolling ball" algorithm[19] segment by thresholding the molecule from the background and measuring molecular fluorescence intensities and length.

*Mesoplasma florum* Preparation. *M. florum*[20] was grown in ATCC 1161 at 30° C. then pelleted. Cells were washed with a solution of 10 mM Tris-HCl, pH 7.6, and 1 M NaCl then pelleted and resuspended. Warmed cells, 37° C., were mixed with 1:1 (v/v) with 1% low melting temperature agarose and dispensed in an insert tray. Inserts[21,22] were pooled in a 50 mL conical tube and incubated in 6 mM Tris-HCl pH 7.6, 1 M NaCl, 100 mM EDTA, 1% N-lauroylsarcosine, and 20 ng/mL RNase, overnight at 37° C. Inserts were then transferred to 0.50 M EDTA pH 8.0, 1% N-lauroylsarcosine, with 1 mg/mL Proteinase K and incubated overnight at 50° C. followed by 0.1 mM phenylmethylsulfonyl fluoride then dialyzed 10 times with 0.50 M EDTA, pH 9.5. Inserts were twice dialyzed against 1×TE, then dialyzed in 0.1×TE for electroelution.

Determination of Surface Charge Density. Surface charge density was estimated using electroosmotic flow measurement in the nanoslit device with two ports. Electroosmotic flow was measured in a setup similar to that described by Huang et al.[23] Ports were cut into an oxygen plasma treated nanoslit device with a standard razor blade. Platinum electrodes, spaced 20 mm apart, were placed in the ports and connected to an EC-105 power supply (EC Apparatus Corporation) with a 195Ω resistor, between second reservoir and the ground. A multimeter was connected directly across the resistor to measure the potential drop as an external electrical potential was applied. Twenty millimolar phosphate buffer, pH 7.0, was added to load and flush the system then 10 mM phosphate buffer pH 7.0 is added, followed by application of ~100 V (3 min); the voltage polarity was then reversed for an additional 3 min. A linear fit identified the intercept (time, t) between the forward and reverse bias for each set of experiments. The electroosmotic mobility ($\mu_{EOF}$) was calculated by $$\mu_{EOF} = \frac{L_C}{Et} \qquad (1)$$

where $L_c$ is the microchannel length, E is the electric field, and t is time.

From the electroosmotic mobility, the charge density on a surface ($\sigma_e$) is $$\sigma_e = \zeta\varepsilon\varepsilon_0\kappa\,\exp(r_w\kappa) \qquad (2)$$

where $\zeta$ is zeta potential, $\kappa^{-1}$ is Debye length, $r_w$ is the normal distance from the surface, $\varepsilon$ the relative permittivity, and $\varepsilon_0$ is the permittivity of a vacuum. Accordingly, the surface density of the device interior was found to be 1.1 to 1.3 e/nm².

Bead Diffusion under Nanoconfinement. YG carboxyl terminated beads (24 nm; Molecular Probes) in 0.20 mM and 10 mM NaCl, =22 and 3 nm, respectively) within nanoslits were imaged using Total Internal Reflection Fluorescence Microscopy (TIRF) microscopy using a Zeiss TIRF 100×1.46 NA objective and 135TV inverted microscope. The optical train comprised: 488 nm illumination (argon-ion laser, Coherent); quarter wave plate; Galilean telescope (40 mm and 200 mm focal length lenses (Edmund Industrial Optics)); broadband filter 485/20 (Semrock); and 525/50 excitation filter (Chroma); beam was then mapped by a 125 mm field length convex lens onto the objective. TIRF excitation produced a penetration depth of ~70 nm (less than nanoslit depth; 100 nm); images passed through a 525/50 emission filter (Chroma) onto an Andor iXon-888 camera, running Andor SOLIS software, which were then background subtracted with a "rolling ball" algorithm for shading correction;[19] a Kalman stack algorithm was implemented to decrease image noise. The periodicity of bead fluorescence intensity fluctuations was analyzed using a Fast Fourier Transform (FFT) for discerning maxima peaks.

DNA Model and Simulation Approach

Figure 2:
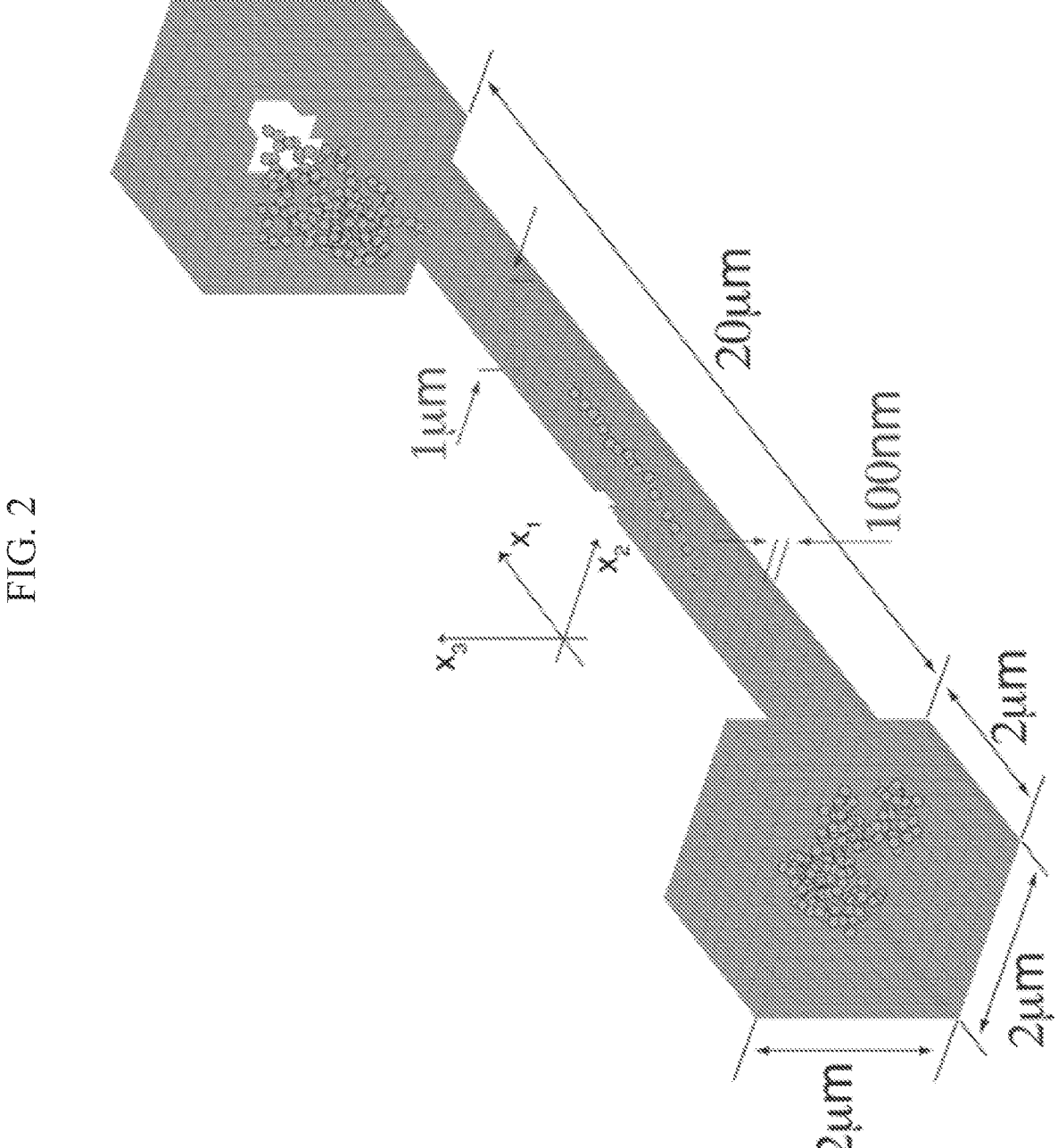
FIG. 2 shows simulated nanoslit geometry. An snapshot of a T4-DNA molecule (166 kb, L=74.5 urn) forming a dumbbell is shown. Simulated slit lengths were 10, 20, and 30 μm; the results were equivalent due to the fact that the molecule stretch is independent of molecular weight. The results presented here were calculated using a 20 urn long nanoslit.

Brownian dynamics (BD) simulations were performed to simulate the DNA dumbbell conformation within the nanoslits. Long-range hydrodynamic interactions were included through a Green's function formalism and calculated with the O(N) General Geometry Ewald-like Method (GGEM).[24-31] There is a combination of confinement effects for the dumbbell conformation. A molecule in a slit experiences a de Gennes' regime (confinement size ~$R_g$)[32] in the microchannel, and within the nanoslit width, an Odijk regime (confinement size ~$l_p$)[16,33,34] in the nanoslit height. This combination of regimes places a number of restrictions on the model to be used to describe the slits considered in this work (see FIG. 2).

Available descriptions of DNA range from detailed atomistic models,[35] to mesoscale models that use multiple sites to define a nucleotide,[36-39] to coarse grained models that describe multiple nucleotides in terms of individual beads (and springs).[40-42] Notable examples include the Kratky-Porod model with a continuous worm-like chain (WLC) model, bead-spring models that use Marko and Siggia interpolation,[43-47] and nonlinear elastic spring (FENE)-based models.[26,27,48] The appropriate model must resolve the length scales of the nanoconfinement without a finite discretization of the persistence length, because characteristic times for segmental diffusion are several orders of magnitude smaller than characteristic chain-diffusion times. Kratky-Porod or higher resolution models are computationally demanding (there is a time scale separation of 8 orders of magnitude between the bead and chain diffusion times). At the other end of the spectrum, a continuous WLC model describing 10-20 persistence lengths in terms of a single spring does not have the resolution required to describe nanoslit confinement.

Yeh et al.[17] performed simulations of bead-spring chains connected by springs to describe their experiments on DNA dumbbells. Starting from a WLC representation of the springs, however, they modified the law until agreement was observed between the model and experiments. It is unclear, however, whether such an approach would be able to describe large DNA molecules over a wide range of conditions and whether it would be truly predictive. A good compromise, and one that we adopt in this work, is provided by the Underhill-Doyle (UD) model.[49-51] The UD model was originally developed for a θ-solvent; in this work we include excluded volume forces and hydrodynamic interactions to describe good-solvent conditions and to generate Zimm scaling. The polymer molecule, dissolved in a viscous solvent, is represented by a bead-spring chain consisting of $N_b$ beads connected through $N_s = N_b - 1$ springs. The conditions of our confined systems are such that the Reynolds number is zero, and inertia is neglected. The force balance on each bead requires $$f_\iota^h + f_\iota^s + f_\iota^v + f_\iota^w + f_\iota^b = 0, \text{ for } \iota = 1, \ldots, N_b \qquad (3)$$

for bead 1, $$f_\iota^h$$

is the hydrodynamic force, $$f_\iota^v$$

is the bead-to-bead excluded volume force, $$f_\iota^w$$

is the bead-wall excluded volume force, $$f_\iota^b$$

$f_\iota^b$ is the Brownian force, and $$f_\iota^s$$

is the UD spring force.

This model, developed using a constant stretch mechanical ensemble, is used for the connectivity between adjacent molecule beads. This model is defined as follows:[49-51]

$$f^s = [a_1(1-\hat{r}^2)^{-2} + a_2(1-\hat{r}^2)^{-1} + a_3 + a_4(1-\hat{r}^2)]x \qquad (4)$$

where $\hat{r} = r/q_0$, $q_0$ is the maximum spring extension, and $r = |x|$, $x = (x,y,z)$.

The coefficients of this polynomial expansion are defined by $$a_1 = 1.0 \qquad (5)$$

$$a_2 = -7\chi \qquad (6)$$

$$a_3 = \frac{3}{32} - \frac{3}{4}\chi - 6\chi^2 \qquad (7)$$

$$a_4 = \frac{(13/32) + (0.8172\chi) - (14.79\chi^2)}{1 - (4.225\chi) + (4.87\chi^2)} \qquad (8)$$

where $$\chi = N_{p,s}^{-1}$$

and $N_{p,s}$ is the number of persistence lengths per spring.

In the development of the model, Underhill and Doyle[49] did an error estimation of the spring law as a function of $N_{p,s}$, and found that it reproduces DNA behavior with a maximum error of 1% for $N_{p,s} \geq 4$. We selected the maximum length resolution of the UD model given by $N_{p,s} = 4$.

For the nonbonded bead-bead interactions, we use a Gaussian excluded volume potential. Neutron scattering data for dilute solutions of linear polymers in good solvent conditions indicate ideal chain behavior at small distances along the chain and good solvent behavior at long distances.[52-57] We consider the increase in energy due to the overlap of two submolecules (or molecular blobs). Each submolecule is considered to have a Gaussian probability distribution with second moment $$S_s^2 = N_{p,s} l_p^2 / 6,$$

where $N_{p,s}$ is the number of persistence lengths per spring. Considering the energy penalty due to overlap of two Gaussian coils, one arrives at the following expression for the excluded volume potential between two beads of the chain:[53,55]

$$\Phi^v = \frac{1}{2} k_B T \omega_v N_{p,s}^2 \left(\frac{3}{4\pi S_S^2}\right)^{3/2} \exp\left[\frac{-3r^2}{4S_S^2}\right] \qquad (9)$$

where $f^v = -\nabla\Phi^v$, $\omega_v$ is the excluded volume parameter related to the DNA effective diameter,[54,55] $k_B$ is the Boltzmann constant, and T is the temperature.

A repulsive Lennard-Jones potential[58,59] is used to describe bead-wall excluded volume interactions, where the Euclidean distance is replaced by the wall normal direction.

The dynamics of the bead-spring DNA molecules are described by evolving the configurational distribution function. The diffusion equation for that function has the form of a Fokker-Planck equation; the force balance described above corresponds to the following system of stochastic differential equations of motion for the bead's positions:[55,60,61]

$$dR = \left[U_0 + \frac{1}{k_B T} D \cdot F + \frac{\partial}{\partial R} \cdot D\right] dt + \sqrt{2} B \cdot dW \qquad (10)$$

where R is a vector containing the $3N_b$ coordinates of the beads that constitute the polymer chain, with $x_i$ denoting the Cartesian coordinates of bead 1.

The vector $U_0$ of length $3N_b$ represents the unperturbed velocity field, i.e., the velocity field in the absence of any polymer molecule. The vector F has length $3N_b$, with $f_l$ denoting the total non-Brownian, nonhydrodynamic force acting on bead 1. Finally, the $3N_b$ independent components of dW are obtained from a real-valued Gaussian distribution with zero mean and variance dt. The motion of a bead of the chain perturbs the entire flow field, which in turns influences the motion of other beads. These hydrodynamic interactions (HI) enter the polymer chain dynamics through the 3×3 block components ($D_{l\mu}$) of the $3N_b \times 3N_b$ diffusion tensor, $D = k_B T M$ (M is the mobility tensor), which may be separated into the bead Stokes drag and the hydrodynamic interaction tensor, $\Omega_{l\mu}$;

$$D_{l\mu} = \left[\frac{\delta}{\xi}\delta_{l\mu} + (1 - \delta_{l\mu})\Omega_{l\mu}\right] \qquad (11)$$

Here $\delta$ is a 3×3 identity matrix, $\delta_{\mu\mu}$ is the Kronecker delta, and is the bead friction coefficient. The Brownian perturbation is coupled to the hydrodynamic interactions through the fluctuation-dissipation theorem: $D=B \cdot B^T$. The characteristic length, time, and force scales describing the system are set by the bead hydrodynamic radius a, the bead diffusion time $\xi a^2/k_B T$, and $k_B T/a$, respectively. The bead friction coefficient $\xi$ is related to the solvent viscosity $\eta$ and a through Stokes' law, i.e., $\xi=6\pi\eta a$.

In conventional Green's function-based methods, M is computed explicitly; the resulting matrix-vector operation to determine the fluid velocity requires $O(N^2)$ operations. Additionally, for nonperiodic domains, appropriate boundary conditions must be included in order to correctly calculate the velocity; for example, u(x)=O for no-slip boundaries. Jendrejack et al.[2,57,62-64] enforced the boundary conditions with solutions using finite element methods (FEMs), where the quadratic scaling limits analysis to small systems. Hernandez-Ortiz et al.[65] generalized a method developed by Mucha et al.[66] that scales as $O(N^{1.66} \log N)$, but is restricted to slit geometries. There are other approaches that allow the calculation of M·F by O(N log N) calculations in periodic domains. For instance, there are Ewald sum and particle-mesh Ewald (PME) methods that are based on the Hasimoto[67] solution for Stokes flow driven by a periodic array of point forces. In this work, the fluid velocity (M·F) is calculated using the O(N) GGEM introduced by Hernandez-Ortiz et al.[25-31,68] GGEM yields M·F without explicit construction of M and, when combined with Fixman's[69,79] midpoint integration algorithm and Fixman's[71] Chebyshev polynomial approximation for B·dW, it allows us to evolve the chains in time through an efficient O(N) matrix free formulation.[26-29] Details of this method and its implementation are described below.

The ionic strength influences DNA conformations through electrostatic interactions between the charges on the DNA phosphate backbone and interactions with nanoslit walls. These interactions are screened over the Debye length $(\kappa^{-1})$, defined by $\kappa^2=2N_A e^2//\epsilon_0 \epsilon k_B T$ (where $N_A$ is Avogadro's number, e is the electronic charge, I is the ionic strength, $\epsilon_0$ is the permittivity of free space, and $\epsilon$ is the dielectric constant of water). As the Debye length increases (from 10 to 30 nm) due to the decrease in ionic strength (1.0 to 0.11 mM), the persistence length of the molecule increases due to backbone like-charge repulsions, and due to the decrease in the effective height of the channel (which is in turn due to surface-DNA charge repulsions). Odijk[34] and Skolnick and Fixman[72] (OSF) have estimated theoretically how the persistence length $(l_p)$ of a worm-like polyelectrolyte coil is affected by a short-ranged electrostatic potential. Baumann et al. confirmed their theoretical predictions through experiments on large DNA molecules,[73] achieving a quantitative prediction with an expression of the form $$l_p = l_{p,0} + \left( \frac{0.0324M}{I} \right) nm \qquad (12)$$

where $l_{p,0}$ is the intrinsic persistence length corresponding to fully screened electrostatic contributions $(l_{p,0}=50 \text{ nm})$.

In our experiments, the persistence length of the dumbbell molecules ranges from 82.4 to 358 nm. Although predictions of the OSF theory have raised concerns,[74] OSF is known to give the correct scaling for the persistence length with respect to the ionic strength.[73,75] As alluded to earlier, the ionic environment also plays a major role in the confinement because the surface of the device has a charge density of 1.1 to 1.3 $e/nm^2$, with its own Debye length. Our BD simulations do not include electrostatic interactions with the walls directly; instead, the model was parameterized to account for the change in persistence length, and the wall-excluded volume was modified according to the Debye length. Note that we are currently implementing a full HI-electrostatic DNA model to account for these effects more accurately, and results will be presented in the future. The model parameterization was performed using experimental data for λ-DNA in the bulk; we use L=21 μm, $R_g$=0.7 μm, (S)=1.5 μm, $l_p$=53 nm at l=10.798 mM, and a Zimm diffusion coefficient (HI chains) of Dz=0.0115 $\mu m^2/s$ in a 43.3 cP solvent at 23° C. (Note that the actual viscosity $(_s)$ is much lower).

Scaling arguments were then used to find the model parameters at different ionic strengths:

$$R_g \sim L^{3/5} l_p^{1/5} \omega^{1/5} \text{ and } D_Z \sim \eta_S^{-1} R_g^{-1} \qquad (13)$$

where $\omega \sim \kappa^{-1}+\kappa^{-1} \log(V_{eff}\kappa^{-1})$ is the effective diameter of DNA,[76,77] and $V_{eff}$ is an effective DNA line charge[78,79]. The UD model was subsequently parametrized to produce the necessary scaling dictated by the ionic strength and persistence length; thus, the range of the bead-bead excluded volume was modified to $$\omega l_p^2$$

to follow the scaling given in eq 13,[54] while the bead-wall excluded volume range was increased in order to account for the wall Debye length.

Theoretical Considerations on Nanoconfined DNA Dumbbells

An analytical theory is used to provide interpretation for the dynamical behavior of the nanoconfined DNA molecules.

Free Energy of a Lobe. If we momentarily neglect the opening of the nanoslit, we may view the DNA chain within one lobe of the dumbbell as a long flexible coil of contour length s restricted by a hard smooth wall. The partition function of a coil with two ends fixed is known to be given by a Gaussian function in free space minus its mirrored version induced by an image charge[80-82] (if the chain is ideal). This is because its value must reduce to zero at the wall. Integrating over the configuration of one end point, one derives the partition function G(z;s), where z is the distance of the other end of the lobe to the wall and the lobe consists of s/A Kuhn segments of length $A=2l_p$. G is actually a function of $z/s^{1/2}A^{1/2}$ only which for $z<<s^{1/2}A^{1/2}$ reduces to[81]

$$G(z; s) = \left( \frac{2z^2}{\pi s A} \right)^{1/2} \qquad (14)$$

The area of the opening of the nanoslit is D×h (h<<D). Equation 14 is strictly valid if z>h. Here, $h=O(l_p)$, so the DNA within the nanoslit (with zero or few back folds) is joined to the lobe with z>~h by a short intervening section of DNA whose description is challenging. The free energy of the latter maybe neglected, however, so the free energy of the lobe is expressed as $$F_l(z;s)=-k_B T \ln G(h;s)=\text{constant}-k_B T \ln h+\tfrac{1}{2}k_B T \ln s \qquad (15)$$

If the DNA of total contour length L translocates through a nanopore instead of a nanoslit, eq 15 then leads to a total free energy $$F_L = \text{constant} + \tfrac{1}{2}k_B T \ln(L-s)s \tag{16}$$

as argued by Sung and Park.[83]

If the lobes are asymmetric, there is a force $$f_l = -\frac{\partial F_L}{\partial s} = -\frac{(L-2s)k_B T}{2(L-s)s} \tag{17}$$

on the DNA driving it out of the nanopore. A similar force should play a dominant role when the DNA translates through a nanoslit in the deflection regime, provided there are two lobes. The effect of excluded volume is rather weak; it merely changes the numerical coefficient in eq 15.[81]

Symmetrical Dumbbell. It is of interest to study the equilibrium of the symmetrical dumbbell. If we suppose the nanoslit is long and we neglect electrostatics, we may write the total free energy of the DNA $$F_{Total} = k_B T \ln s + \frac{l_s^2 k_B T}{4g(L-s)} \tag{18}$$

from eq 15.

We have added an ideal chain term for the stretched DNA spanning the nanoslit of length $$l_s(l_s^2 \gg gL).$$

A long chain slithers back and forth along the channel and has a global persistence length $g \ll l_s$. Therefore, the force on the DNA $$f_s = -\frac{\partial F_{Total}}{\partial s} = -\frac{k_B T}{s} - \frac{l_s^2 k_B T}{4g(L-s)^2} \tag{19}$$

is never equal to zero; an exactly symmetrical dumbbell conformation cannot exist in equilibrium.

The two lobes must retract into the nanoslit. The counterintuitive nature of the free energy of a single lobe has been emphasized before by Farkas et al.[84] An isolated chain experiences a deflection force away from a wall (s is constant but z becomes larger in eq 14). However, for a lobe attached to a section of DNA within the nanoslit, z=h is held fixed and s is variable. We note that the entropic force arising from the lobes in eq 19 is generally quite weak.

Excluded-Volume Effect and Nondraining Limit. How well do the physical properties of the DNA samples used in FIG. 6 conform to asymptotic regimes? The excluded volume parameter $z_{el}$ is a measure of the excluded-volume effect between two Kuhn segments[85]

$$z_{el} = 0.183\omega L^{1/2} l_p^{-3/2} \tag{20}$$

where the DNA effective diameter is $\omega=74.9$ nm at I=0.51 mM.

The total persistence length equals 113.5 nm from eq 12. Hence, $z_{el}$ ranges from 2.5 to 5.0 for the DNA samples in FIG. 6 (molecule sizes ranging from 146 to 582 kb). The excluded volume effect may regarded as close to asymptotic ($z_{el} \gg 1$).

If a DNA molecule is regarded as a wormlike chain with a hydrodynamic diameter d≈2 nm, the draining properties depend on the parameters $L/2l_p$ and $d/2l_p \approx 0.01$. Yamakawa and Fujii have developed a theory for the translational friction coefficient in their classic work.[86] Here, the DNA coils turn out to be long enough so that their hydrodynamics is, effectively, in the nondraining limit.

Nanoconfinement-Mediated Ejection. In the case where there is only a single lobe, the DNA is ejected from the nanoslit because there is a substantial free energy difference between the nanoconfined DNA and its equivalent in the remaining lobe.[87-89] Burkhardt computed the coefficient $C_1$ in the expression for the free energy of a DNA chain in a nanoslit numerically.[90]

$$F_{cL} = \frac{C_1 k_B T x}{l_p^{1/3}}\left(D^{-2/3} + h^{-2/3}\right) \tag{21}$$

where $C_1=1.1036$ and x=L−s. This clearly often overwhelms the contribution from the lobe (eq 15) and the force $f_s=-\partial F_{cL}/\partial x$ on the chain is constant.

The DNA is forced out of the nanoslit; the force f must overcome the hydrodynamic friction on the DNA, which may be viewed effectively as a straight rod under the ionic conditions imposed here. The coefficient of friction in the longitudinal dimension may be written as[53]

$$\zeta_\parallel \approx \frac{2\pi\eta_s x}{\ln(h/d)} \tag{22}$$

This is independent of D because the upper cutoff in the hydrodynamics is the smaller scale h, which itself is much larger than d. Therefore to a first approximation, the equation of motion of the sliding DNA may be expressed as $$\zeta_\parallel(t)\frac{dx(t)}{dt} = -f_s \tag{23}$$

The lobe increases in size as the DNA is ejected, but the frictional force on it may be neglected in eq 23. From the previous section, we know its size R(s) scales as $s^{3/5}$ so that we have dR/dt=−3/5 (R(t)/s(t)) dx(t)/dt. Moreover, in the nondraining limit, the coefficient of friction on the expanding lobe is $r_1 R(t)$ so the lobe friction is a higher order term. Another issue is how well bulk hydrodynamics applies within the slit. There is evidence for a possible breakdown of this assumption for very tight silica nanoslits (h equal to about 20 nm)[91,92] In our case, the PDMS nanoslits, which are less tight, are also expected to be smoother although we feel a thorough investigation of the magnitude of the friction is warranted in the future.

Equation 23 is readily solved and leads to a parabolic equation as has been presented before[87-89]

$$x^2 = l_s^2\left(1 - \frac{t}{\tau_s}\right) \tag{24}$$

-continued $$\tau_s = \frac{\pi \eta_s l_s^2}{|f_s| \ln(h/d)} \tag{25}$$

It has been assumed that the DNA fills the entire nanoslit at t=0. If we set h=0.1 μm, D=1 μm, $l_p$=0.1135 μm, L=28 μm, $\eta_s$=1 cP, and d=2 nm, we compute a force $|f_s|$=13 $k_B$T/m and an ejection time $\tau_s$=12 s. The latter agrees well with the time the T4 DNA molecule is ejected from the nanoslit in experiments. A tentative conclusion is that bulk hydrodynamics indeed applies within the nanoslit. By contrast, the experimental friction on the DNA in the square silica nanochannels of Mannion et al.[89] was found to be five times higher than predicted by an expression analogous to eq 22. This discrepancy is unexplained.

Lobe Translocation. Numerous computational and analytical studies have been devoted to the translocation of a flexible polymer chain through a nanopore, as has been reviewed recently.[93] In our experiments, the DNA stretch is very high within the nanoslit, so we think it is plausible that the translocation dynamics of the DNA lobe should be quite similar to that in a nanopore device. A full analysis of all chain fluctuations will be needed to bear this out in the future.

Often the time $\tau_l$ a chain needs to translocate through a nanopore scales as a power law in terms of the number of segments N, i.e., $$\tau_l \sim N^\beta \tag{26}$$

A main objective has been to compute β precisely, but this has engendered considerable controversy.[93] This is beyond the scope of this work, although we have summarized several representative predictions for β in Table 1.

TABLE 1

| Exponent β of the Lobe Translocation Time $\tau_l \sim$ $N^\beta$ as a Function of the Number of Segments $N^a$ | | |
|---|---|---|
| unbiased | free-draining | nondraining |
| without memory effects | $1 + 2\nu = 2.2^{94}$ | $3\nu = 1.8^{94}$ |
| with memory effects | $2 + \nu = 2.6^{95}$ | $1 + 2\nu = 2.2^{95}$ |
| forced | free-draining | nondraining |
| without memory effects | $2\nu = 1.2^{97}$ | $3\nu - 1 = 0.8^{97}$ |
| with memory effects | $(1 + 2\nu)/(1 + \nu) = 1.38^{97}$ | $3\nu/(1 + \nu) = 1.13^{97}$ |

$^a$In forced translocation, the time is inversely proportional to the force.
The excluded-volume exponent ν is chosen here to be equal to ⅗.

In the case of unbiased translocation, Chuang et al.[94] argued that the polymer chain cannot be viewed as a single particle diffusing across an entropic barrier given by eq 15. The diffusion through the nanopore is collective and Rouse-like across a distance R~$s^\nu$, the size of the lobe. The translocation time ti should then scale as $NR^2(N) \sim N^{1+2\nu}$ (see entry in Table 1). With hydrodynamic interactions, the frictional factor proportional to N reduces to $N^\nu \sim R$.

Recently, it has been proposed that this simple scenario should be amended.[95] The presence of the nanopore (or nanoslit) implies the dynamics of translocation is strongly inhomogeneous. The diffusion of segments across the pore causes an imbalance in tension between the two lobes. The translocation time affected by these memory effects becomes effectively longer (see Table 1).

When the extending force f on a lobe is large enough (f R(s)>$k_B$T), the translocation becomes forced, and $\tau_l$ is inversely proportional to f. We have corroborated the entry in Table 1 for the case without memory effects because it disagrees with an earlier estimate.[96] Our argument is based on the rate of dissipation dF/dt. On the one hand, this equals the velocity of the chain $V_i$ at the opening of the nanopore times the force f reeling the lobe in. In view of the fact that the radius of the lobe R~$s^\nu$, we know that $V_i$=−ds/dt=−(s/vR) dR/dt. On the other hand, the rate of dissipation in the Rouse limit within the contracting lobe is given by N$f_0$(dR/dt), where $f_0$=$\zeta_0$(dR/dt) is the typical force on a segment with a friction coefficient of $\zeta_0$. The typical velocity of a segment is dR/dt. The two rates must be identical, thus leading to the entry in Table 1. Memory effects give rise to nontrivial exponents[97] also presented in Table 1.

Results and Discussion

Dumbbell Formation Completely Stretches DNA Molecules and Requires Hydrodynamic Considerations. Using experimental and simulation approaches, we explored the idea that elastic and hydrodynamic contributions to DNA stretch, originating from the coil itself (a dumbbell lobe), in addition to contributions from just nanoconfinement, would greatly enhance DNA elongation. We created DNA dumbbells within our nanoslit device, shown in FIG. 1, by strategically threading DNA molecules through nanoslits, using carefully timed electrical pulses. Conditions were adjusted allowing DNA ends to occupy the two microchannels bounding nanoslit entrances creating dumbbell lobes comprising random coils. DNA stretch within nanoslit portions of the device is estimated by fluorescence intensity measurements comparing nanoslit versus microchannel portions of the same molecule: S/L=$l_s f_m/S_m f_s$; where $f_m$ is the integrated fluorescence intensity of the entire molecule, $f_s$ and $I_s$ are the fluorescence intensity and length of the molecular portion within a slit, and $S_m$ is the known length of the molecule (μm; dye corrected).

Figure 3:
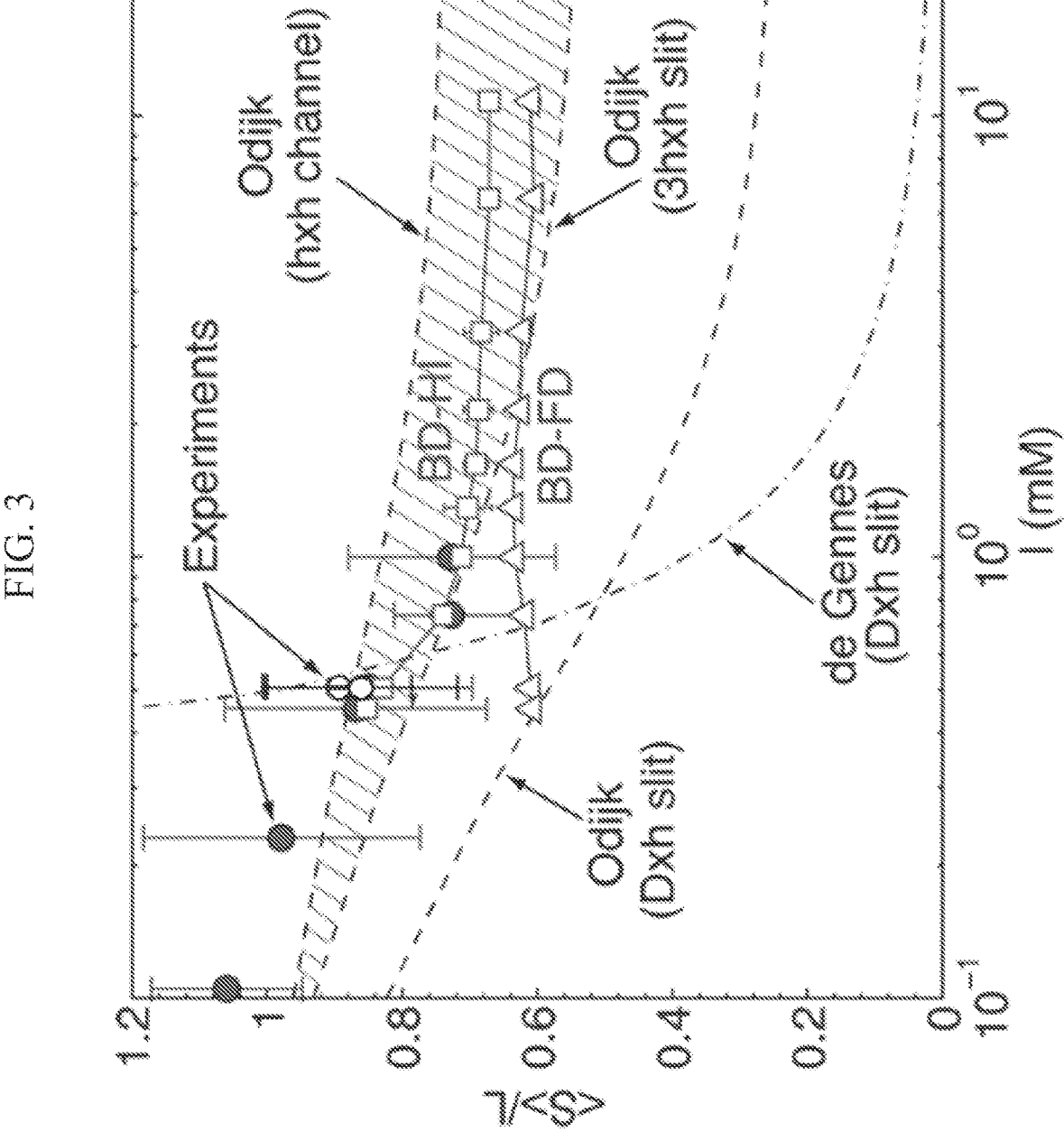
FIG. 3 describes a stretch as a function of ionic strength for T4 DNA (grey bullets (●); error bars show SD on means, N=51-101 molecules) dumbbells showing good concordance between experiments, simulation, and Odijk theory. White bullets (●) show λ concatemer data from FIG. 5, and measurements using an internal standard (see text). Successive dilutions of 1×TE buffer varied ionic strength: 1.0, 0.74, 0.51, 0.45, 0.23, and 0.11 mM. Triangles (Δ) show results from BD simulations without considering hydrodynamic interactions (FD). Boxes (□) show results from BD simulations with fluctuating hydrodynamics interactions (HI). Dotted lines correspond to de Gennes and Odijk scaling predictions. The shaded region encompasses the Odijk scaling between an effective h×h channel and a 3h×h slit.

We expect ionic strength affecting DNA stretch by the electrostatic contributions to persistence length, or polymer stiffness, and the electrostatic environment presented by the device.[5] Accordingly, we evaluated these collective effects on DNA stretch by varying the buffer ionic strength enveloping both sample and device. FIG. 3 shows DNA stretch, using T4 and λ-bacteriophage DNA, as a function of ionic strength, I∈[0.11, 1.0] mM from experiments and from BD simulations (I∈[0.5, 10] mM; see Materials and Experimental Methodology). As the ionic strength decreases, DNA stretch within a nanoslit increases, as previously reported by Jo et al.[5] Here, however, the additional coupling of dumbbell elastic forces greatly enhance DNA stretch by a substantial 37% (S/L=0.85±0.16; I=0.51 mM) over molecular nanoconfinement without dumbbells (S/L=0.62±0.08; I=0.47 mM). Further reduction of ionic strength enables presentation of fully stretched (S/L=1.06±0.19; I=0.11 mM) DNA molecules. We further validate these stretch estimations using λ-DNA as an internal fluorescence standard of known size, within slits, for normalizing integrated fluorescence intensities of λ-concatamer DNA dumbbells (confined portions): (0.87±0.14, N=231; I=0.48 mM), which is similar to the previous value found for T4 DNA (0.85±0.16; I=0.51 mM). The stretch values found for T4 and λ experiments agreed (FIG. 3), indicating consistency and reproducibility of the stretch measurement approaches.

FIG. 3 also shows the results of our theoretical predictions by BD simulations, as compared to experiments. For completeness, results are shown for calculations that include fluctuating hydrodynamic interactions (HI), and calculations when such interactions are neglected (free-draining model, FD). Note that part of the chain is in the nanoslit, and here, HI are expected to be screened and play a minor role. However, as the results in FIG. 3 indicate, HI significantly contributes to the dumbbell dynamics and greatly influences molecular stretch. This can be explained by the fact that Zimm dynamics of the lobes in the microchannel (outside the slit) influence the dynamics of chain segments within the intervening nanoslit. Two trends are discernible in the simulation results: for I>1.0 mM the stretch is nearly constant, and for I≤0.74 mM a sudden increase is observed. Within this latter range, the persistence length of the chain reaches values comparable to the nanoslit height (~100 nm), thereby placing the level of confinement in the Odijk regime. Note that the confinement size, at these ionic strength conditions, is smaller than 100 nm because the walls have their own ion cloud. At this point, the underlying physics becomes complicated due to interactions between the ion clouds associated with the chain and walls. However, one major effect is the reduction of the effective confinement size, i.e., the chain persistence length increases and the "free" available space between the walls decreases. Our simulations of stretch follow the experimentally observed trends, but slightly under-predict (≤5%) the experimental data. We attribute the discrepancy to the fact that full electrostatic interactions are not included in our model. Also note that it is not possible to use the current model for the two lowest ionic strength conditions considered in experiments because the persistence length is higher than the confinement ($l_p$>100 nm). These points aside, the simulations reveal the underlying physical phenomena behind dumbbell-mediated stretch, and most importantly, the critical interplay between HI acting at the lobes and the electrostatic interactions helping to confine and elongate DNA molecules.

Figure 4:
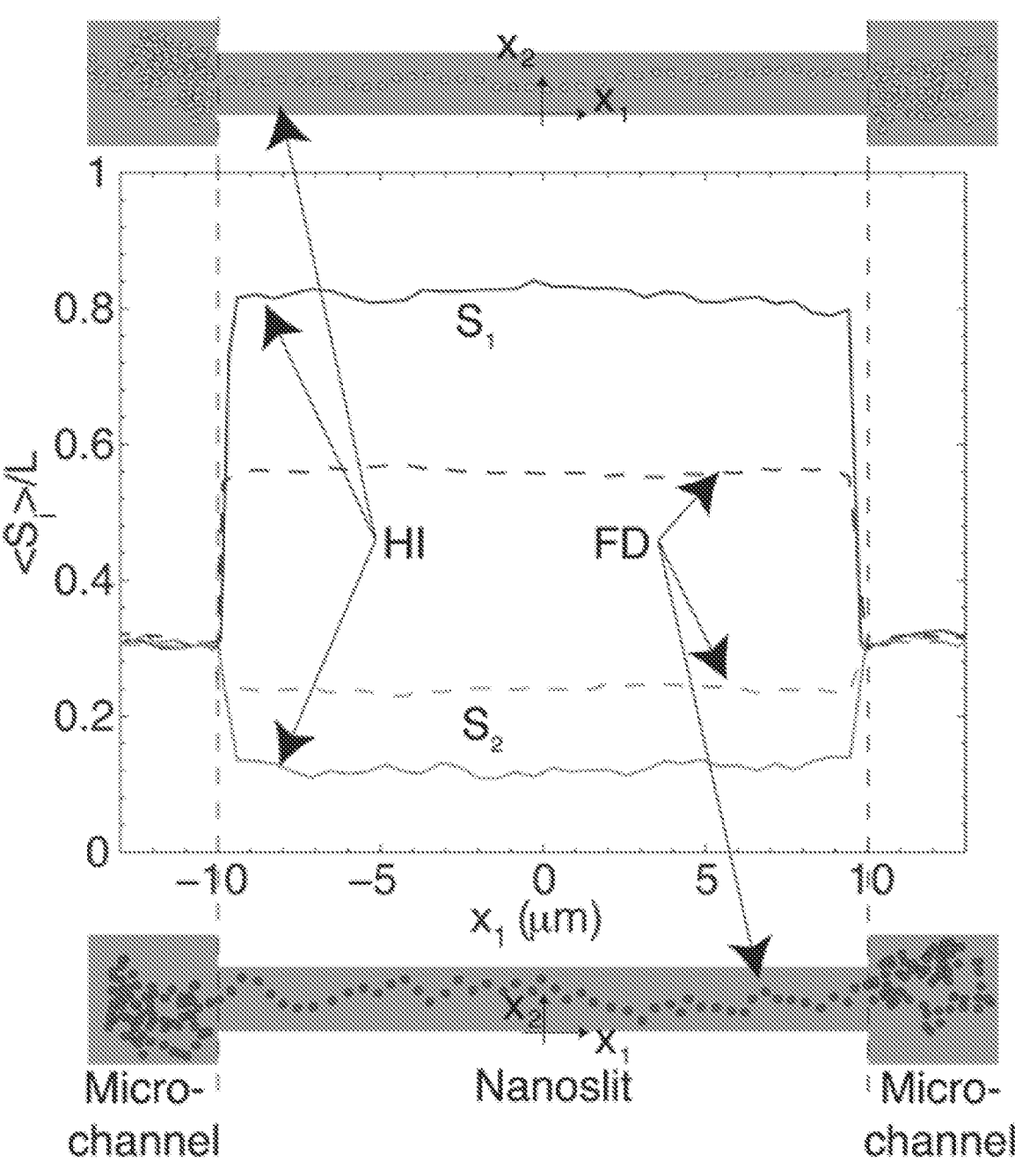
FIG. 4 is a stretch along the nanoslit axial and width directions as a function of nanoslit axial position for T4 DNA dumbbells at I=0.51 mM. The predicted stretches are shown for HI (continuous lines) and FD (dotted lines) chains. Snapshots of an HI chain (top) and an FD chain (bottom) are included.

FIG. 4 provides a comparison of molecular stretch in different directions, both in the presence and absence of HI. Outside the nanoslits, the stretch in all directions, $S_1$ (axial), $S_2$ (perpendicular) and $S_3$ (confinement) is in the range 30-32% (where $S_i$=|max($x_i$)−min($x_i$)|$_i$, for the ith direction of the chain 1). Thus, $S_i$ is the distance between the two segments of the chain having the longest separation in each direction. In contrast, the segment inside the nanoslits exhibits distinct differences in the three directions when HI are included. First, the stretch in the axial direction, $S_1$, is always higher with HI than without (FD chains). The HI $S_1$ stretch is always around 5-7% below the total stretch, indicating that it is the major contributor to the total stretch. The FD $S_1$ stretch, on the other hand, remains constant with ionic strength in the range 55-60%. The $S_2$ stretch in the nanoslits, in the perpendicular direction, is in the range 20-25% without HI (FD chains); similar to that observed outside the nanoslit. The HI $S_2$ stretch inside the nanoslits is 10-15%. This change in the perpendicular stretch indicates a clear difference between the HI and FD molecular conformations within the nanoslits. The FD chains do not "feel" the dumbbell lobes, thereby allowing the chain to perform a pseudorandom walk in the nanoslit width direction (bottom chain in FIG. 4); in contrast, HI dumbbells exhibit a "collective" behavior that increases the stretch in the axial direction and impedes the chain from moving freely in the nanoslit width direction; the net result is the creation of a "rigid" dumbbell (top chain in FIG. 4). To summarize, the dumbbell conformation leads to elongation of DNA molecules within a pseudonanochannel. Electrostatic interactions, enhanced by our low ionic strength conditions, accentuate the confinement of DNA molecules. Note that Debye lengths range from 3 nm at 11 mM to 30 nm at 0.11 mM. Importantly, at low ionic strength, the Debye length is comparable to the nanoslit height, an effect that cannot be overlooked.[98] This electrostatic effect, combined synergistically with collective HI and nanoconfinement, greatly enhances DNA stretch.

Debye Length Considerations. Given these simulation results, which highlight electrostatic contributions by the device walls to DNA stretch, we experimentally investigated how the Debye length affects nanoconfinement[99] by studying the diffusion kinetics of negatively charged latex beads (24 nm) within nanoslits using TIRF microscopy (see Materials and Experimental Methodology). The idea is that bead diffusivity would be measurably perturbed, as a function of ionic strength, due to the accrued Debye lengths of the device (22 nm, I=0.20 mM; 3 nm, I=10 mM) and the beads (24 nm). The average periodicity was measurably different for 0.1997 mM and 9.987 mM NaCl, namely, 8±3 s and 12±4 s, respectively (N=16 beads), thereby implying that the Debye length effectively limits the height of the nanoslit (i.e., bead diffusion is more confined at lower ionic strengths). These observations confirm the sudden decrease of chain motilities in the confined direction, once the ionic strength is decreased. Simulated DNA motility (diffusion) in the confined direction was ~90 nm at the higher ionic strength conditions, which shifted to a very small 1-5 nm at lower ionic strength conditions.

Figure 5:
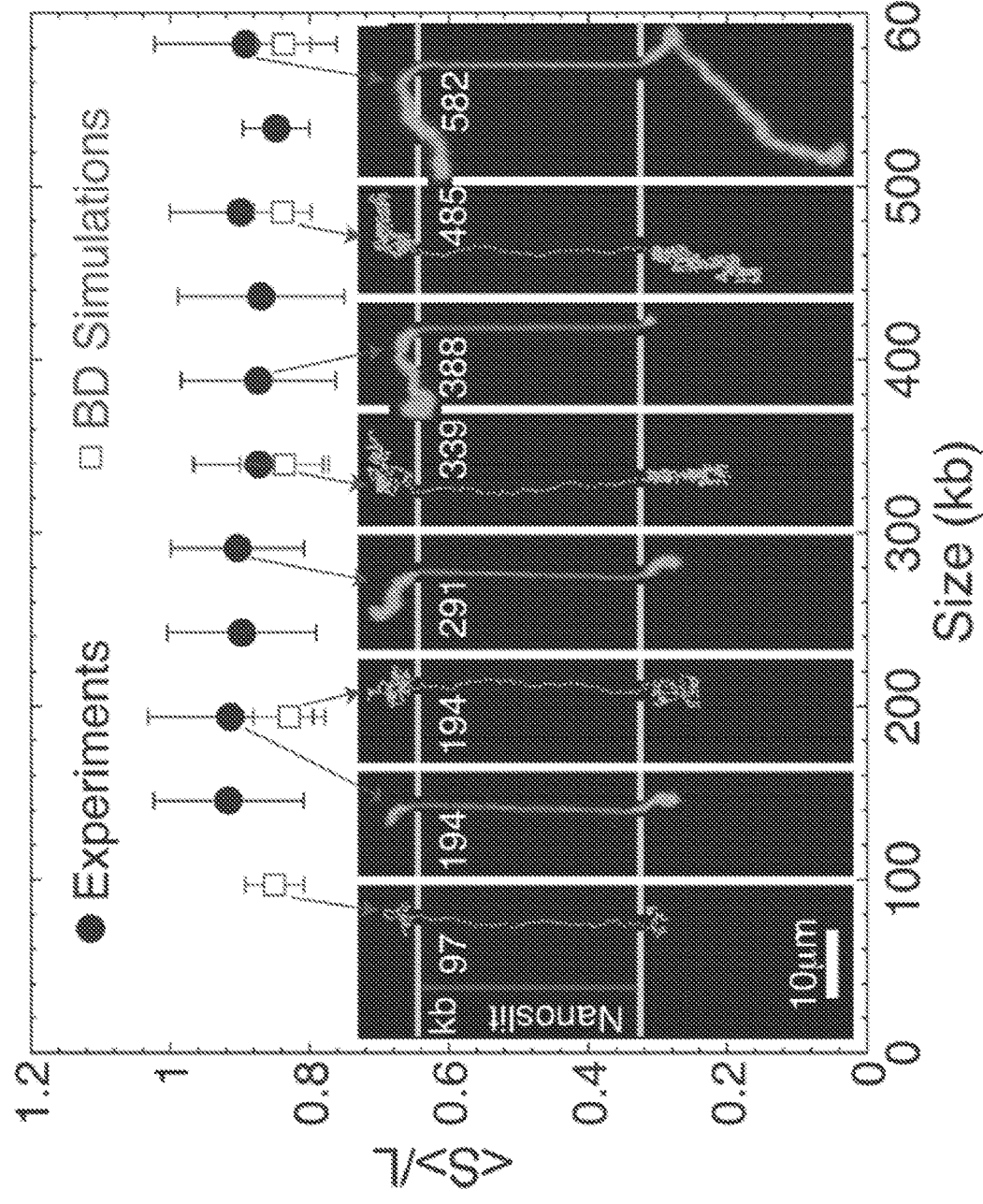
FIG. 5 is a stretch of λ-DNA concatemer dumbbells as a function of size: experiment compared to BD simulation. Arrows link experimental and simulation results to graphical outputs and a montage of micrographs; error bars show SD on the means (dots) for N=9-93 molecules. Cartoon shows a vertical line delineating a nanoslit; horizontal lines indicate nanoslit boundaries. Dumbbell lobes enlarge with increasing molecular size for a given slit/microchannel geometry and show a compelling similarity to simulation.

How DNA Size Affects Dumbbell Stretching and Relaxation Time. FIG. 5 shows DNA stretch as a function of molecular size (97 kb-582 kb; I=0.51 mM), using a series of λ concatemers. Note that the same device can be used for uniform presentation of molecules of any size, once the molecule contour length exceeds twice the nanoslit length for ensuring confident dumbbell formation. In the figure, experimental and simulated results are included. For a dumbbell conformation, we calculate the mean squared variation of the axial position of chain segments within the nanoslit. Importantly, this mobility indicates how reliable an optical measurement of labeled DNA features is inside the nanoslit; the simulation results show a mobility of 150±20 bp for I=11 mM, and 100±20 bp for I=0.51 mM. We note that ultimately the two lobes of the dumbbell do not stabilize the conformation, even when the dumbbell is symmetric (see the Theoretical Considerations section).

Figure 6:
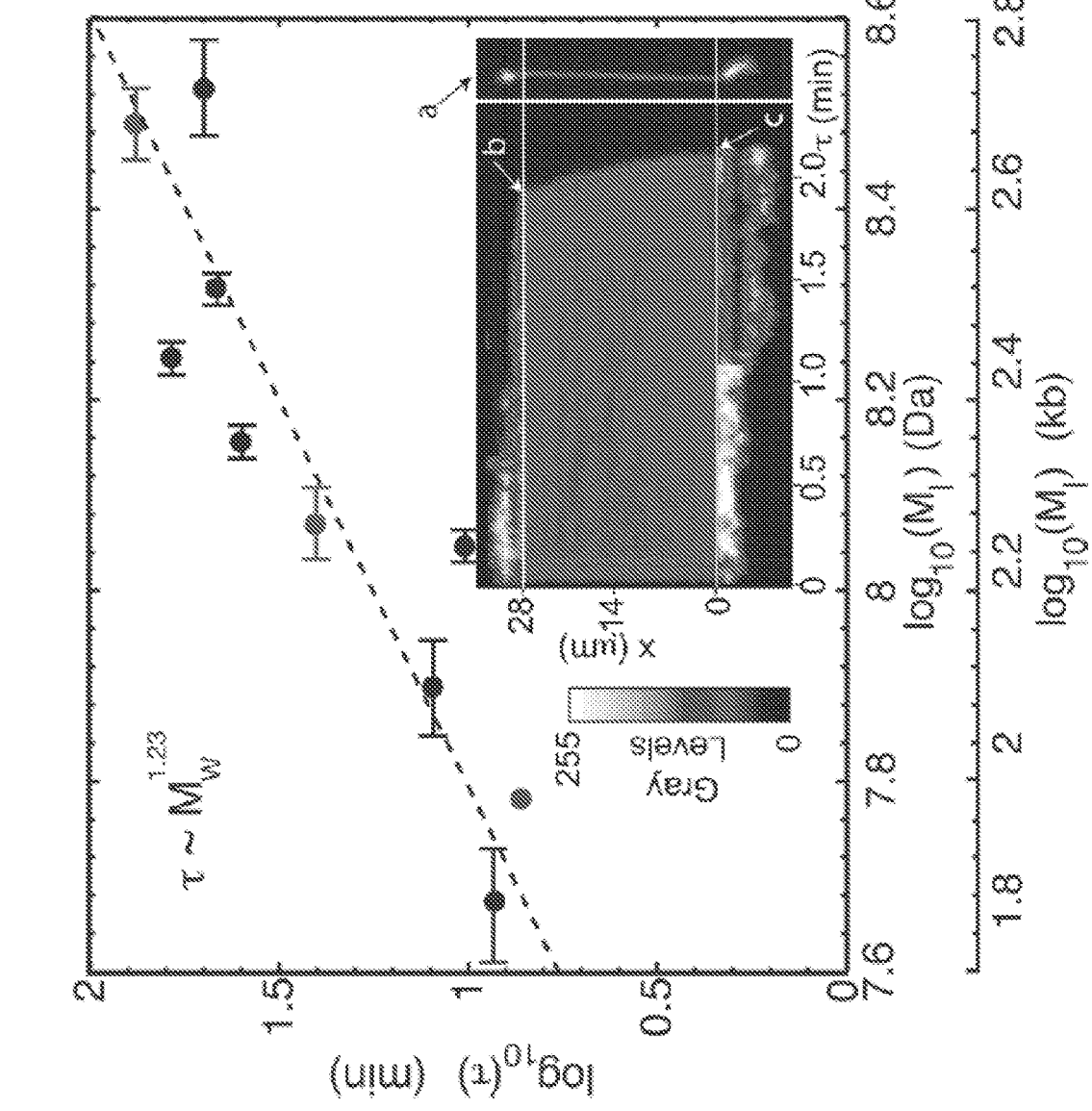
FIG. 6 shows dumbbell relaxation times as a function of molecule size for T4 (white bullets (●), N=105 molecules), λ-DNA concatemers (black bullets (●), N=4-21 molecules), and M. florum DNA (grey bullets (●), N=11-59 molecules) digested with the restriction enzyme Apal. Each circle represents a mean relaxation time (R$_t$) for a given molecule size (146 kb-582 kb; x-axis error bars show 95% confidence intervals). Linear regression fit to the log-log plot shows an exponent of 1.23±0.09 (R$^2$=0.82). The exponent error is determined with a consistency test that includes each point's mean and x-axis error. (Inset) Dumbbell dynamics for a T4 DNA molecule imaged as a movie shown here as compiled time slices (arrow a shows one slice; 0.440 s per slice).

The effective relaxation time of dumbbell molecules was analyzed by loading the molecules in the same manner as in the stretching experiments. In the dynamical experiments, however, some molecules had to be imaged over a 7 h time course using attenuated illumination to prevent photocleavage, which would destroy dumbbells. Bright dumbbell lobes are thresholded in the image data for their analysis, leaving invisible the connecting DNA backbones within the nanoslits. The last time point at which a molecule was observed determined the relaxation time of a dumbbell within a slit; we then averaged all relaxation times for a given molecular size, irrespective of relative lobe size. Molecules remaining after completion of measurements were checked for spurious surface-attachment by applying an electrical field; adhered molecules are not included in our data sets. Also, molecules ≤1.00 kb were excluded because they formed small lobes that rapidly relaxed. The relaxation time is the translocation time of a single DNA lobe plus the ejection time of the DNA chain out of the nanoslit. The latter time turns out to be quite short, typically about 10 s. This agrees well with our theoretical estimate of 12 s based on entropic ejection; the viscosity of the aqueous solvent inside the nanoslit would appear to be close to that of the bulk. The ejection time is a simple, minor correction, which we have subtracted from the relaxation time. The resulting translocation times are plotted in FIG. 6 for the λ concatemers (black), T4 (white), and *M. florum* (grey) DNA molecules. The dependent variable is not the actual molecular mass of the DNA molecules, but the molecular mass of the two lobes of the dumbbell (Ml) because we have subtracted the DNA mass within the nanoslit from this. This correction is significant for the lower masses. In FIG. 6, we have fitted the lobe translocation time with a power law $\tau \sim Ml^{1.23}$ (If we had plotted the original relaxation times, the exponent would have been 1.71). The dumbbell lobe fluorescence intensities fluctuate over time until one lobe slips into the nanoslit (arrow b), then the molecule transits the nanoslit into the bottom microchannel and exits into the microchannel (arrow c). The details of the inset of FIG. 6 for purposes of this application are less critical than understanding that the inset is a time lapse of the above-described motion.

Our exponent 1.23 rules out unbiased translocation (see Table 1, where we also show that the DNA chains are effectively nondraining and the excluded-volume effect is quite fully exerted). It is comparable with the exponent 1.13 predicted for forced translocation with hydrodynamic interactions in the nanopore case.[97] At present, it is, however, difficult to rule out a theory of translocation without memory effects. In the bulk, the frictional properties of a long DNA chain may be nondraining. However, the polymer conformations are strongly inhomogeneous for a lobe attached to a nanoslit or nanopore. It may be argued that a portion of the chain conforms to Rouse dynamics, so the predicted exponent would be somewhere between 0.8 and 1.2 (Table 1). Our exponent 1.23 also appears to agree with the value 1.27 measured by Storm et al.[100-102] for DNA translocating through a silicon-oxide nanopore. However, their ionic strength was high (I=1 M), so the excluded volume was weak and their chains were close to ideal (v=½ in Table 1). Our own (unpublished) analysis shows that the top lobe in FIG. 6 is indeed being translocated into the nanoslit under an external force, which appears to be constant. The origin of this force is obscure at present; it cannot be of entropic origin as discussed in the Theoretical Considerations, for this force is much too weak. These mild forces lead to lengthy translocation and relaxation times.

There is some debate or confusion in the literature[11,103-105] regarding the transition between de Gennes and Odijk confinement regimes. The set of experiments presented here help clarify one issue in that debate, because they have been performed at very low salt concentrations. The decrease of ionic strength has two major consequences: an increase of the chain persistence length, and an enhanced, effective confinement induced by the Debye length of the device's surface. Our experimental observations show that once the effective confinement is equal to the chain persistence length the Odijk regime is achieved. This feature apparently contradicts other conclusions,[11] which suggested that the effective DNA diameter, ω, has a major effect on the de Gennes-Odijk transition. However, the contradiction is apparent because the ionic strength in ref[11] is much higher than used here. Wang et al.[106] have attempted to show how the results of ref.[11] fit in with the intermediate regimes. FIG. 3 includes the stretch predictions of de Gennes theory (S/L~(ωl$_p$)$^{1/3}$ (Dh)$^{-1/3}$) and Odijk theory (S/L~1−[(D/l$_p$)$^{2/3}$+(h/l$_p$)$^{2/3}$]), for D=1 μm×h=100 nm nanoslit. Initially, one may infer from the figure that the experiments do not follow any scaling regime; however, we must recall that the dumbbell conformation emulates nanochannel confinement. In other words, the DNA dumbbells "feel" an effective, lower channel width. Once this effect is included, the experiments follow the Odijk predictions that the shadow region encompasses (FIG. 3); namely, an Odijk prediction for a 3h×h nanoslit and for a h×h channel. As pointed out by T. Odijk,[16,33,34] his theory does not include severe electrostatic interactions; accordingly, his method will slightly under-predict stretch at the lower ionic strength conditions considered here. We are currently developing an improved molecular model to account for full electrostatic interactions.[25] Once the dumbbells are formed and the molecule is presented in a fully stretched manner, a natural question is to examine the mobility of the chains within the nanoslit and the dumbbell's relaxation time. However, the dumbbell dynamics reported here show relaxation times that will support genomic analysis schemes using imaging, which require consistently stretched DNA molecules. The addition of sucrose to the low ionic strength solutions and the decrease of temperature (i.e., shifted after loading) would increase solution viscosity and extend the relaxation time of dumbbell molecules.

Modern genome analysis demands long-range sequence information that is uniquely presented by large DNA molecules. As such, the findings presented here, using tightly coupled experimental and simulation approaches, have provided an experimental and theoretical infrastructure for the design and implementation of the newer genome analysis systems. These advances may provide the means for fully leveraging the informational advantages intrinsically offered by very long DNA molecules in ways that will greatly enhance our understanding of genome structures.

APPENDIX

General Geometry Ewald-like Method and O(N) Algorithm[25-31] The fluid velocity M·F is calculated using the O(N) GGEM introduced by Hernandez-Ortiz et al.[28] A brief description of the GGEM starts with considering the Stokes system of equations for a flow driven by a distribution of N$_b$ point forces, $$-\nabla p(x) + \eta \nabla^2 u(x) = -\rho(x)$$

$$\nabla \cdot u(x) = 0$$

where η is the fluid viscosity and the force density is $$\rho(x) = \sum_{l=1}^{N_b} f_l \delta(x - x_l) \tag{28}$$

where f$_l$ is the force exerted on the fluid at point x$_l$.

The solution of 27 can be written in terms of a Stokeslet[28,107] and combined into the M·F product. If computed explicitly, this product is a matrix-vector operation requiring O(N$^2$) calculations. GGEM determines the product implicitly for any geometry (with appropriate boundary conditions) without performing the matrix-vector manipulations. It starts with the restatement of the force-density expression in eq 27, $\rho(x) = \rho_l(x) + \rho_g(x)$ using a smoothing function g(x), similar to conventional particle-mesh Ewald methods.[108-110] This screening function satisfies $$\int_{all\ space} g(x)dx = 1 \tag{29}$$

By linearity of the Stokes equation, the fluid velocity is written as a sum of two parts, with separate solutions for each force-density. The "local density"

$$\rho_l(x) = \sum_{l=1}^{N_b} f_l [\delta(x - x_l) - g(x - x_l)] \tag{30}$$

drives a local velocity, $u_l(x)$, which is calculated assuming an unbounded domain:

$$u_l(x) = \sum_l^{N_b} G_l(x - x_l) \cdot f_l \tag{31}$$

where $G_l(x)$ is composed of a free-space Greenis's function, or Stokeslet, minus a smoothed Stokeslet obtained from the solution of Stokes equations with the forcing term modified by the smoothing function $g(x)$.

For the Stokes equations, we found that a modified Gaussian smoothing function defined by $$g(r) = \frac{\alpha^3}{\pi^{3/2}} e^{(-\alpha^2 r^2)}\left(\frac{5}{2} - \alpha^2 - r^2\right) \tag{32}$$

yields a simple expression for $G_l(x)$:

$$G_l(x) = \frac{1}{8\pi\eta}\left(\delta + \frac{xx}{r^2}\right)\frac{\text{erfc}(\alpha r)}{r} - \frac{1}{8\pi\eta}\left(\delta - \frac{xx}{r^2}\right)\frac{2\alpha}{\pi^{1/2}} e^{(-\alpha^2 r^2)} \tag{33}$$

Because $G_l(x)$ decays exponentially on the length scale $\alpha$-1, in practice the local velocity can be computed, as in conventional Ewald methods, by only considering near-neighbors to each particle 1.[58,111]

For the present work, the point-particle approximation is not desired; in particular, as the chain size increases, the probability that particles will overlap, having un-physical velocities, increases. To avoid this problem, the bead hydro-dynamic radius, a, can be used to define a new smoothed-force density that gives a non-singular velocity. This is achieved by replacing the Stokeslet by a regularized Stokeslet, using the same modified Gaussian with a replaced by $\xi$ with $\xi \cdot a^{-1}$, yielding $$G_l^R(x) = \frac{1}{8\pi\eta}\left(\delta + \frac{xx}{r^2}\right)\left[\frac{\text{erf}(\xi r)}{r} - \frac{\text{erf}(\alpha r)}{r}\right] + \tag{34}$$
$$\frac{1}{8\pi\eta}\left(\delta - \frac{xx}{r^2}\right)\left(\frac{2\xi}{\pi^{1/2}} e^{(-\xi^2 r^2)} - \frac{2\alpha}{\pi^{1/2}} e^{(-\alpha^2 r^2)}\right)$$

where the superscript R stands for regularized force density. For $\xi^{-1} = 3a/(\pi)^{1/2}$, the maximum fluid velocity is equal to that of a particle with radius a and the pair mobility remains positive-definite.[28,112]

The global velocity, $u_g(x)$, is due to the force distribution $\rho_g(x)$, which is given by $$\rho_g(x) = \sum_{l=1}^{N_b} f_l g(x - x_l) \tag{35}$$

For a general domain, we find the solution to Stokes' equation numerically, requiring that $u_l(x) + u_g(x)$ satisfy appropriate boundary conditions. At a no-slip boundary, we would require $u_g(x) = -u_l(x)$. For problems with periodic boundary conditions, Fourier techniques can be used to guarantee the periodicity of the global velocity $u_g(x)$. The periodicity on the local velocity, $u_l(x)$, is obtained using the minimum image convention.

In the present case, the global contribution is solved with a FEM formulation, where 8-nodded brick elements[27,113] are used for the velocity and constant elements are used for the corresponding global pressure. The solution of the linear system is done through a fast LU decomposition solver for sparse matrices, SUPER-LU.[114,115] The LU decomposition of the matrix is only done at the beginning of the simulation; during the time advancement, the only necessary computation is the back-substitution, making the GGEM algorithm highly efficient ($\sim O(N)$, given the sparse characteristic of the matrix). Given the fact that the GGEM solution is independent of $\alpha$, the appropriate selection of this parameter is based on the optimization of the computational time. In the global calculation, to reach an accurate solution, the mesh size must be smaller than the scale of the smoothing function, which is $\alpha^{-1}$. Therefore, the mesh resolution scales as $M \sim \alpha^3$; the cost of each back-substitution scales as $M^2$, leading to a total global cost that scales as $\alpha^6$. In the local calculation, the contribution of all pairs that lie within a neighbor list determined by the decay of the local Green's function must be calculated. The local Green's function decays over a distance $\alpha^{-1}$, so the number of neighbors for each particle scales as $N\alpha^{-3}$. The calculation must be performed over all pairs, which is the number of particles times the number of neighbors per particle, resulting in a local calculation cost that scales as $N^2\alpha^{-3}$. Minimizing the total (local and global) computational cost with respect to a gives an optimal a that scales as $\alpha_{opt} N^{2/9}$ and a total cost that scales as $O(N^{4/3})$. If we had chosen a different, linear, method for the solution (GMRES, Bi-conjugate methods[116]), the global cost would have scaled as $\alpha^3$, leading to an optimal value of $\alpha_{opt} \sim N^{1/3}$ and a total computational cost that would scale as $O(N)$.

Because GGEM yields $M \cdot F$ without explicit construction of M, it is desirable to time-integrate eq 10 without requiring this product, i.e., a "matrix-free" formulation. Fixman[69,70] proposed a method to time-integrate this system without needing to evaluate $\partial/\partial R \cdot D$:

$$R^* = R(t) - \frac{1}{2}[U_0(R) + M(R) \cdot F(R)]\Delta t + \frac{1}{2}$$
$$\sqrt{2}D(R)B^{-1}(R) \cdot \Delta W(t)$$

$$R(t+\Delta t) = R(t) + [U_0(R^*) + M(R^*) \cdot F(R^*)]\Delta t + \sqrt{2}D(R^*)B^{-1}(R) \cdot \Delta W(t) \tag{36}$$

The only remaining step is to evaluate $B^{-1} \cdot dW$ in a matrix-free way. As also noted by Fixman,[71] this can be done by a Chebyshev polynomial approximation method that requires only matrix-vector products, not the matrix itself. This approach has already been implemented in unbounded or periodic domains;[26-28,30,62,64,117,118] with GGEM it can be directly generalized to arbitrary domains.

The present invention has been described in terms of one or more preferred embodiments, and it should be appreciated that many equivalents, alternatives, variations, and modifications, aside from those expressly stated, are possible and within the scope of the invention.

REFERENCES (1) Dimalanta, E.; Lim, A.; Runnheim, R.; Lamers, C.; Churas, C.; Forrest, D.; de Pablo, J.; Graham, M.; Coppersmith, S.; Goldstein, S.; Schwartz, D. Anal. Chem. 2004, 76, 5293-5301.

(2) Jendrejack, R. M.; Dimalanta, E. T.; Schwartz, D. C.; Graham, M. D.; De Pablo, J. J. Phys. Rev. Lett. 2003, 91, 038102.

(3) Teague, B.; et al. Proc. Natl. Acad. Sci. U.S.A. 2010, 107, 10848.

(4) Antonacci, F.; Kidd, J. M.; Marques-Bonet, T.; Teague, B.; Ventura, M.; Girirajan, S.; Alkan, C.; Campbell, C. D.; Vives, L.; Malig, M. Nat. Genet. 2010, 42, 745-750.

(5) Jo, K.; Dhingra, D.; Odijk, T.; De Pablo, J.; Graham, M.; Runnheim, R.; Forrest, D.; Schwartz, D. Proc. Natl. Acad. Sci. U.S.A. 2007, 104, 2673.

(6) Valouev, A.; Li, L.; Liu, T. C.; Schwartz, D. C.; Yang, Y.; Zhang, Y.; Waterman, M. S. J. Comput. Chem. 2006, 13, 442-462.

(7) Valouev, A.; Schwartz, D. C.; Zhou, S.; Waterman, M. S. Proc. Natl. Acad. Sci. U.S.A. 2006, 103, 15770.

(8) Valouev, A.; Zhang, Y.; Waterman, M. S.; Waterman, M. S. Bioinformatics 2006, 22, 1217-1224.

(9) Kim, Y.; Kim, K. S.; Kounovsky, K. L.; Chang, R.; Jung, G. Y.; de Pablo, J. J.; Jo, K.; Schwartz, D. C. Lab Chip 2011, 11, 1721.

(10) Das, S. K.; Austin, M. D.; Akana, M. C.; Deshpande, P.; Cao, H.; Xiao, M. Nucleic Acids Res. 2010, 38, e177-e177.

(11) Reisner, W.; Beech, J. P.; Larsen, N. B.; Flyvbjerg, H.; Kristensen, A.; Tegenfeldt, J. O. Phys. Rev. Lett. 2007, 99, 058302.

(12) Reisner, W.; Morton, K.; Riehn, R.; Wang, Y.; Yu, Z.; Rosen, M.; Sturn, J.; Chou, S.; Frey, E.; Austin, R. Phys. Rev. Lett. 2005, 94, 196101.

(13) Reccius, C.; Mannion, J.; Cross, J.; Craighead, H. Phys. Rev. Lett. 2005, 95, 268101.

(14) Reccius, C.; Stavis, S.; Mannion, J.; Walker, L.; Craighead, H. Biophys. J. 2008, 95, 273.

(15) Mannion, J.; Reccius, C.; Cross, J.; Craighead, H. Biophys. J. 2006, 90, 4538.

(16) Odijk, T. Macromolecules 1983, 16, 1340.

(17) Yeh, J.-W.; Taloni, A.; Chen, Y.-L.; Chou, C.-F. Nano Lett. 2012, 12, 1597-1602.

(18) Abramoff, M.; Magelhaes, P.; Ram, S. J. Biophotonics Int. 2004, 11, 36.

(19) Sternberg, S. Computer 1983, 16, 22.

(20) Mesoplasma florum Sequencing Project. Broad Institute: www.broad.mit.edu.

(21) Herschleb, J.; Ananiev, G.; Schwartz, D. C. Nature Protocols 2007, 2, 677.

(22) Schwartz, D. C.; Cantor, C. R. Cell 1984, 37, 67.

(23) Huang, X.; Gordon, M. J.; Zare, R. N. Anal. Chem. 1988, 60, 1837-1838.

(24) Geier, S.; Hernandez-Ortiz, J. P.; de Pablo, J. J. Chem. Ing. Tech. 2011, 83, 900-906.

(25) Hernandez-Ortiz, J. P. Dyna (Medellin, Colomb.) 2012, 79, 105.

(26) Hernandez-Ortiz, J. P.; Chopra, M.; Geier, S.; de Pablo, J. J. Chem. Phys. 2009, 131, 044904.

(27) Hernandez-Ortiz, J. P.; Ma, H.; Pablo, J. J. D.; Graham, M. D. Korea-Aust. Rheol. J. 2008, 20, 143-152.

(28) Hernandez-Ortiz, J. P.; de Pablo, J.; Graham, M. D. Phys. Rev. Lett. 2007, 98, 140602.

(29) Hernandez-Ortiz, J. P.; Underhill, P. T.; Graham, M. D. J. Phys.: Condens. Matter 2009, 21, 204107.

(30) Miller, C.; Hernandez-Ortiz, J. P.; Abbott, N. L.; Gelman, S. H.; de Pablo, J. J. J. Chem. Phys. 2008, 129, 015102.

(31) Pranay, P.; Anekal, S. G.; Hernandez-Ortiz, J. P.; Graham, M. D. Phys. Fluids 2010, 22, 123103.

(32) Brochard, F.; de Gennes, P. G. J. Chem. Phys. 1977, 67, 52-56.

(33) Odijk, T. Phys. Rev. E 2008, 77, 060901.

(34) Odijk, T. J. Polym. Sci. B: Polym. Phys. 1997, 15, 477.

(35) Mergell, B.; Ejtehadi, M.; Everaers, R. Phys. Rev. E 2003, 68, 021911.

(36) Knotts, T. A.; Rathore, N.; Schwartz, D. C.; de Pablo, J. J. J. Chem. Phys. 2007, 126, 084901.

(37) Sambriski, E. J.; Ortiz, V.; Pablo, J. J. D. J. Phys.: Condens. Matter 2009, 21, 034105.

(38) Sambriski, E. J.; Schwartz, D. C.; de Pablo, J. J. Biophys. J. 2009, 96, 1675.

(39) Sambriski, E. J.; Schwartz, D. C.; de Pablo, J. J. Proc. Natl. Acad. Sci. U.S.A. 2009, 106, 18125.

(40) Locker, C. R.; Fuller, S. D.; Harvey, S. C. Biophys. J. 2007, 93, 2861.

(41) Locker, C. R.; Harvey, S. C. Multiscale Model. Simul. 2006, 5, 1264.

(42) Petrov, A. S.; Lim-Hing, K.; Harvey, S. C. Structure 2007, 15, 807.

(43) Bustamante, C.; Marko, J. F.; Siggia, E. D.; Smith, S. Science 1994, 265, 1599.

(44) Marko, J. F.; Siggia, E. D. Macromolecules 1995, 28, 8759.

(45) Marko, J. F.; Siggia, E. D. Macromolecules 1994, 27, 981.

(46) Chen, Y.-L.; Graham, M. D.; de Pablo, J. J.; Randall, G. C.; Gupta, M.; Doyle, P. S. Phys. Rev. E 2004, 70, 060901(R).

(47) Chen, Y.-L.; Graham, M. D.; de Pablo, J. J.; Jo, K.; Schwartz, D. C. Macromolecules 2005, 38, 6680.

(48) Hernandez-Ortiz, J. P.; Ma, H.; de Pablo, J. J.; Graham, M. D. Phys. Fluids 2006, 18, 123101.

(49) Underhill, P. T.; Doyle, P. S. J. Rheol. 2006, 50, 513.

(50) Underhill, P. T.; Doyle, P. S. J. Rheol. 2005, 49, 963.

(51) Underhill, P. T.; Doyle, P. S. J. Non-Newt. Fluid Mech. 2004, 122, 3.

(52) Farnoux, B.; Bou, F.; Cotton, J. P.; Daoud, M.; Jannink, G.; Nierlich, M.; de Gennes, P. G. J. Phys. (Paris) 1978, 39, 77.

(53) Doi, M.; Edwards, S. The Theory of Polymer Dynamics; Oxford University Press: Oxford, U. K., 1986.

(54) Rubinstein, M.; Colby, R. Polymer Physics; Oxford University Press: Oxford, U. K., 2003.

(55) Ottinger, H.-C. Stochastic Processes in Polymeric Fluids; Springer: Berlin, 1996.

(56) Strobl, G. R. The Physics of Polymers; Springer-Verlag: Berlin, 1997.

(57) Jendrejack, R. M.; de Pablo, J. J.; Graham, M. D. J. Chem. Phys. 2002, 116, 7752-7759.

(58) Allen, M.; Tildesley, D. Computer Simulation of Liquids; Oxford Science Publications: Oxford, U. K., 1987.

(59) Frenkel, D.; Smith, B. Understanding Molecular Simulations: From Algorithms to Applications; Academic Press: San Diego, CA, 1996.

(60) Risken, H. The Fokker-Planck Equation, 2nd ed.; Springer: Berlin, 1989.

(61) Gardiner, C. Handbook of Stochastic Methods; Springer: Berlin, 1985.

(62) Jendrejack, R. M.; Schwartz, D. C.; de Pablo, J. J.; Graham, M. D. J. Chem. Phys. 2004, 120, 2513-2529.

(63) Jendrejack, R. M.; Schwartz, D. C.; Graham, M. D.; de Pablo, J. J. J. Chem. Phys. 2003, 119, 1165-1173.

(64) Jendrejack, R. M.; Graham, M. D.; de Pablo, J. J. J. Chem. Phys. 2000, 113, 2894.

(65) Hernandez-Ortiz, J. P.; de Pablo, J. J.; Graham, M. D. J. Chem. Phys. 2006, 125, 164906.

(66) Mucha, P. J.; Tee, S.-Y.; Weitz, D. A.; Shraiman, B. I.; Brenner, M. P. J. Fluid Mech. 2004, 501, 71-104.

(67) Hasimoto, H. J. Fluid Mech. 1959, 5, 317-328.

(68) Hernandez-Ortiz, J. P.; Stoltz, C. G.; Graham, M. D. Phys. Rev. Lett. 2005, 95, 204501.

(69) Fixman, M. J. Chem. Phys. 1978, 69, 1527.

(70) Grassia, P.; Hinch, E.; Nitsche, L. J. Fluid. Mech. 1995, 282, 373.

(71) Fixman, M. Macromolecules 1986, 19, 1204.

(72) Skolnick, J.; Fixman, M. Macromolecules 1977, 10, 944. Natl. Acad. Sci. U.S.A. 1997, 94, 6185.

(73) Baumann, C.; Smith, S.; Bloomfield, V.; Bustamante, C. Proc. Natl. Acad. Sci. U.S.A. 1997, 94, 6185.

(74) Hsieh, C.-C.; Doyle, P. S. Korea-Aust. Rheol. J. 2008, 20, 127-142.

(75) Ullner, M. J. Phys. Chem. B 2003, 107, 8097-8110.

(76) Stigter, D. Biopolymers 1977, 16, 1435-1448.

(77) Stigter, D. J. Colloid Interface Sci. 1975, 53, 296.

(78) Vologodskii, A.; Cozzarelli, N. Biopolymers 1995, 35, 289.

(79) Hsieh, C.-C.; Balducci, A.; Doyle, P. S. Nano Lett. 2008, 8, 1683-1688.

(80) Chandrasekhar, S. Rev. Mod. Phys. 1943, 15, 1.

(81) Eisenriegler, E.; Kremer, K.; Binder, K. J. Chem. Phys. 1982, 77, 6296.

(82) DiMarzio, E. A.; McCrackin, F. L. J. Chem. Phys. 1965, 43, 539.

(83) Sung, W.; Park, P. J. Phys. Rev. Lett. 1996, 77, 783-786.

(84) Farkas, Z.; Derenyi, I.; Vicsek, T. J. Phys.: Condens. Matter 2003, 15, 51767.

(85) Odijk, T. Biopolymers 1979, 18, 3111-3113.

(86) Yamakawa, H.; Fujii, M. Macromolecules 1973, 6, 407-415.

(87) Turner, S.; Cabodi, M.; Craighead, H. G. Phys. Rev. Lett. 2002, 88, 128103.

(88) Milchev, A.; Klushin, L.; Skvortsov, A.; Binder, K. Macromolecules 2010, 43, 6877-6885.

(89) Mannion, J.; Reccius, C.; Cross, J.; Craighead, H. G. Biophys. J. 2006, 90, 4538-4545.

(90) Burkhardt, T. W. J. Phys. A: Math., Nucl. Gen. 1997, 30, 167-172.

(91) Cross, J. D.; Strychalski, E. A.; Craighead, H. G. J. Appl. Phys. 2007, 102, 024701.

(92) Salieb-Beugelaar, G. B.; Teapal, J.; Nieuwkasteele, J.; Wijnperle, D.; Tegenfeldt, J. O.; Lisdat, F.; Van Den Berg, A.; Eijkel, J. C. T. Nano Lett. 2008, 8, 1785-1790.

(93) Milchev, A. J. Phys.: Condens. Matter 2011, 23, 103101.

(94) Chuang, J.; Kantor, Y.; Kardar, M. Phys. Rev. E 2001, 65, 011802.

(95) Panja, D.; Barkema, G. T.; Ball, R. C. J. Phys.: Condens. Matter 2007, 19, 432202.

(96) Kantor, Y.; Kardar, M. Phys. Rev. E 2004, 69, 021806.

(97) Vocks, H.; Panja, D.; Barkema, G. T.; Ball, R. C. J. Phys.: Condens. Matter 2008, 20, 095224.

(98) Stein, D.; Deurvorst, Z.; van der Heyden, F. H. J.; Koopmans, W. J. A.; Gabel, A.; Dekker, C. Nano Lett. 2010, 10, 765-772.

(99) Popov, K. I.; Nap, R. J.; Szleifer, I.; de la Cruz, M. O. J. Polym. Sci., Part B: Polym. Phys. 2012, 50, 852-862.

(100) Storm, A. J.; Chen, J. H.; Zandbergen, H. W.; Dekker, C. Phys. Rev. E 2005, 71, 051903.

(101) Storm, A. J.; Chen, J. H.; Ling, X. S.; Zandbergen, H. W.; Dekker, C. J. Appl. Phys. 2005, 98, 014307-014307-8.

(102) Storm, A.; Storm, C.; Chen, J.; Zandbergen, H.; Joanny, J.; Dekker, C. Nano Lett. 2005, 5, 1193-1197.

(103) Tegenfeldt, J.; Prinz, C.; Cao, H.; Chou, S.; Reisner, W.; Riehn, R.; Wang, Y.; Cox, E.; Sturm, J.; Silberzan, P.; Austin, R. Proc. Natl. Acad. Sci. U.S.A. 2004, 101, 10979.

(104) Micheletti, C.; Orlandini, E. Soft Matter 2012, 8, 10959-10968.

(105) Orlandini, E.; Micheletti, C. J. Biol. Phys. 2013, 39, 267.

(106) Wang, Y.; Tree, D. R.; Dorfman, K. D. Macromolecules 2011, 44, 6594-6604.

(107) Pozrikidis, C. Boundary Integral and Singularity Methods for Linearized Viscous Flow; Cambridge University Press: Cambridge, U.K., 1992.

(108) Deserno, M.; Holm, C. J. Chem. Phys. 1998, 109, 7678.

(109) Deserno, M.; Holm, C. J. Chem. Phys. 1998, 109, 7694.

(110) Essmann, U.; Perera, L.; Berkowitz, M. J. Chem. Phys. 1995, 103, 8577.

(111) Hockney, R. W.; Eastwood, J. W. Computer Simulation Using Particles; Taylor & Francis: Bristol, PA, 1988.

(112) Power, H.; Wrobel, L. C. Boundary Integral Methods in Fluid Mechanics; Computational Mechanics Publications: Southampton, U. K., 1995.

(113) Osswald, T. A.; Hernandez-Ortiz, J. P. Polymer Processing: Modeling and Simulation; Carl Hanser-Verlag: Munich, Germany, 2006.

(114) Demmel, J. W.; Eisenstat, S. C.; Gilbert, J. R.; Li, X. S.; Liu, J. W. H. SIAM J. Matrix Anal. Appl. 1999, 20, 720-755.

(115) Demmel, J. W.; Gilbert, J. R.; Li, X. S. SIAM J. Matrix Anal. Appl. 1999, 20, 915-952.

(116) Press, W. H.; Teukolsky, S. A.; Vetterling, W. T.; Flannery, B. P. Numerical Recipes in Fortran 77, 2nd ed.; Cambridge University Press: Cambridge, U.K., 1992.

(117) Banchio, A. J.; Brady, J. F. J. Chem. Phys. 2003, 118, 10323-10332.

(118) Stoltz, C.; de Pablo, J. J.; Graham, M. D. J. Rheol. 2006, 50, 137.

The invention claimed is:

1. A micro-fluidic device comprising:

a first microchannel;

a second microchannel;

a nanoslit extending between the first and second microchannels, the nanoslit providing a fluid path between the first and the second microchannels, the nanoslit having nanoslit electrostatic or hydrodynamic properties;

a nucleic acid molecule having a first end portion, a second end portion, and a central portion positioned between the first end portion and the second end portion, the nucleic acid molecule having nucleic acid molecule electrostatic or hydrodynamic properties; and an ionic buffer within the nanoslit and the first and second microchannels, the ionic buffer having an ionic strength and a buffer temperature, producing a Debye length;

the first microchannel including a first cluster region adjacent to a first end of the nanoslit and the second microchannel including a second cluster region adjacent to a second end of the nanoslit, the nucleic acid molecule in a dumbbell configuration such that the first cluster region contains the first end portion, the second cluster region contains the second end portion, and the nanoslit contains the central portion, the nucleic acid molecule having a contour length that is greater than a nanoslit length of the nanoslit, and the ionic strength and the buffer temperature of the ionic buffer providing a summed Debye length that is greater than or equal to a nanoslit height or a nanoslit width, wherein the nanoslit height or nanoslit width is the smallest physical dimension of the nanoslit, wherein the summed Debye length, is a function of the ionic strength and the buffer temperature of the ionic buffer, the nanoslit electrostatic or hydrodynamic properties and the nucleic acid molecule electrostatic or hydrodynamic properties, and is four times the Debye length at the given ionic strength and the buffer temperature, wherein central portion of the nucleic acid molecule is fully stretched within the nanoslit by virtue of the summed Debye length being greater than or equal to the nanoslit height or the nanoslit width, the nucleic acid molecule occupying the dumbbell configuration, the nanoslit electrostatic or hydrodynamic properties, and the nucleic acid molecule electrostatic or hydrodynamic properties, wherein the ionic strength is between 0.11 mM to 1.0 mM, wherein the nanoslit width is between 200 nm and 10 μm, and wherein the nanoslit length is less than or equal to half a contour length of the nucleic acid molecule.

2. The micro-fluidic device of claim 1, the nanoslit height is less than or equal to 100 nm.

3. The micro-fluidic device of claim 1, wherein at least one of the microchannels has one or more of the following: a microchannel width of about 20 um, a microchannel length of about 10 mm, and a microchannel height of about 1.66 μm.

4. The micro-fluidic device of claim 1, the device further comprising a temperature adjustment module.

5. The micro-fluidic device of claim 1, wherein the buffer temperature is less than or equal to 20° C.

6. The micro-fluidic device of claim 1, wherein the ionic buffer further comprises a viscosity modifier.

7. The micro-fluidic device of claim 1, wherein the nucleic acid molecule has a relaxation time of at least about 30 seconds.

8. The micro-fluidic device of claim 1, wherein the nucleic acid molecule is a DNA molecule.

9. A method of stretching a nucleic acid molecule in an ionic buffer, the method comprising:

positioning the nucleic acid molecule in a dumbbell configuration such that a central portion of the nucleic acid molecule occupies a nanoslit, a first end portion of the nucleic acid molecule occupies a first cluster region adjacent to a first end of the nanoslit, and a second end portion of the nucleic acid molecule occupies a second cluster region adjacent to a second end of the nanoslit, the nanoslit, the first cluster region, and the second cluster region including the ionic buffer, the nucleic acid molecule having a contour length that is greater than a nanoslit length of the nanoslit, and the ionic buffer having an ionic strength and a buffer temperature, producing a Debye length, the nanoslit having nanoslit electrostatic or hydrodynamic properties and the nucleic acid molecule having nucleic acid molecule electrostatic or hydrodynamic properties, the ionic strength and the buffer temperature providing a summed Debye length that is greater than or equal to a nanoslit height or a nanoslit width, wherein the nanoslit height or nanoslit width is the smallest physical dimension of the nanoslit, wherein the summed Debye length, is a function of the ionic strength and the buffer temperature of the ionic buffer, the nanoslit electrostatic or hydrodynamic properties and the nucleic acid molecule electrostatic or hydrodynamic properties, and is four times the Debye length at the given ionic strength and the buffer temperature, wherein the nucleic acid molecule is fully stretched within the nanoslit by virtue of the summed Debye length being greater than or equal to the nanoslit height or the nanoslit width, the molecule occupying the dumbbell configuration, the nanoslit electrostatic or hydrodynamic properties, and the molecule electrostatic or hydrodynamic properties, wherein the ionic strength is between 0.11 mM to 1.0 mM, and wherein the nanoslit width is between 200 nm and 10 μm, and wherein the nanoslit length is less than or equal to half a contour length of the nucleic acid molecule.

10. The method of claim 9, wherein positioning the nucleic acid molecule includes threading the nucleic acid molecule through the nanoslit.

11. The method of claim 9, wherein positioning the nucleic acid molecule includes electrokinetically driving the central portion of the nucleic acid molecule into the nanoslit.

12. The method of claim 9, wherein the nanoslit height is less than or equal to 100 nm.

13. The method of claim 9, wherein at least one of the microchannels has one or more of the following: a microchannel width of about 20 μm, a microchannel length of about 10 mm, and a microchannel height of about 1.66 μm.

14. The method of claim 9, wherein the buffer temperature is less than or equal to 20° C.

15. The method of claim 9, wherein the ionic buffer further comprises a viscosity modifier.

16. The method of claim 9, wherein the nucleic acid molecule has a relaxation time of at least about 30 seconds.

17. The method of claim 9, wherein the nucleic acid molecule is a DNA molecule.

18. The method of claim 9, the method further comprising imaging at least a portion of the central portion.

* * * * *